United States Patent [19]

Asano et al.

[11] 4,360,663
[45] Nov. 23, 1982

[54] STEROID HORMONE-ANTITUMOR DERIVATIVES

[75] Inventors: Kiro Asano; Humio Tamura, both of Kukizaki; Hiromitsu Tanaka, Tokyo; Satoru Enomoto, Fujisawa, all of Japan

[73] Assignee: Kureha Kagaku Kogyo Kabushiki Kaisha, Tokyo, Japan

[21] Appl. No.: 212,117

[22] Filed: Dec. 2, 1980

Related U.S. Application Data

[62] Division of Ser. No. 62,819, Aug. 1, 1979, Pat. No. 4,260,736.

[30] Foreign Application Priority Data

| Aug. 14, 1978 | [JP] | Japan | 53-98796 |
| Aug. 14, 1978 | [JP] | Japan | 53-98797 |
| Aug. 14, 1978 | [JP] | Japan | 53-98798 |
| Aug. 14, 1978 | [JP] | Japan | 53-98799 |
| Sep. 4, 1978 | [JP] | Japan | 53-108290 |
| Dec. 8, 1978 | [JP] | Japan | 53-152176 |
| Dec. 14, 1978 | [JP] | Japan | 53-154842 |
| May 29, 1979 | [JP] | Japan | 54-66496 |

[51] Int. Cl.$^3$ .............................. C07J 17/00; C07J 3/00
[52] U.S. Cl. .................................... 536/5; 260/397.5
[58] Field of Search .......................... 536/5; 260/397.5

[56] References Cited

U.S. PATENT DOCUMENTS 4,242,332 12/1980 Albrecht et al. ................... 536/5

FOREIGN PATENT DOCUMENTS

| 223397 | 2/1958 | Australia | 260/397.5 |
| 278815 | 12/1964 | Australia | 260/397.5 |
| 286247 | 10/1965 | Australia | 260/397.5 |
| 543766 | 11/1967 | Australia | 260/397.5 |
| 2702509 | 7/1977 | Fed. Rep. of Germany | 260/397.5 |
| 1476179 | 6/1977 | United Kingdom | 260/397.5 |

Primary Examiner—Elbert L. Roberts
Attorney, Agent, or Firm—Oblon, Fisher, Spivak, McClelland & Maier

[57] ABSTRACT

A process for producing a steroid hormone-antitumor derivative which selectively affects to tumor or cancer cells comprises reacting X group of a steroid hormone derivative having the formula

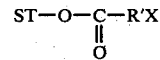

$$ST-O-\underset{\underset{O}{\|}}{C}-R'X$$

wherein ST represents a steroid moiety having a cyclophenanthrene hydrocarbon skeleton of gonane, estrane or androstane which is bound to carboxyl group by esterifying OH group on D ring with carboxyl group; and R' represents a $C_1$-$C_4$ alkylene group and X represents a halogen atom, amino group, hydroxyl group, carboxyl group or a salt thereof, with a modified or non-modified reactive group of an antitumor drug to form a binded group of —O—, —COO—, —CONH—, —NH— or —N—.
　　　　　　　　　　　　　　　　　　　　　　|

5 Claims, No Drawings

STEROID HORMONE-ANTITUMOR DERIVATIVES

This is a division of application Ser. No. 062,819, filed Aug. 1, 1979 now U.S. Pat. No. 4,260,736.

BACKGROUND OF THE INVENTION

1. Field of the Invention

The present invention relates to novel steroid hormone-antitumor derivatives and preparations thereof. More particularly, it relates to a method of modifying an antitumor drug to improve its antitumor effect and to reduce its toxicity by binding the antitumor drug to a carboxylic acid derivative of a specific steroid hormone.

2. Description of the Prior Art

When most of medicines are administrated and transferred in body organs and tissues, a ratio of the medicine transferred to the ill organs or cells is remarkably small whereas a ratio of the medicine decomposed or excreted without reaching to the ill organs or cells is remarkably large. Most of known antitumor drugs destroy tumor or cancer cells and also highly damage normal cells. Therefore, it is difficult to administrate the known antitumor drugs for a long period and it is difficult to completely destroy tumor or cancer cells.

It is remarkably effective on therapeutics, if an antitumor drug selectively affect only to tumor or cancer cells.

The inventors have studies on a method of selectively affecting a physiologically active material to the object organs or cells. As a result, it has been found that steroid hormone-antitumor derivatives obtained by binding a physiologically active material especially an antitumor drug to a steroid hormone derivative are remarkably effective for said objects.

SUMMARY OF THE INVENTION

It is an object of the present invention to provide a method of improving antitumor effect and reducing toxicity by modifying the antitumor drug with a special steroid hormone derivative.

It is another object of the present invention to provide a method of selectively binding a modified or non-modified reactive group of an antitumor drug to a specific steroid hormone derivative.

The foregoing and other objects of the present invention have been attained by providing steroid hormone-antitumor derivatives for selectively affecting to tumor or cancer cells which are obtained by binding X group of a steroid hormone derivative having the formula

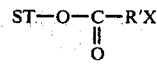

wherein ST represents a steroid moiety having cyclopentanophenanthrene hydrocarbon skeleton such as gonane, estrane or androstane hydrocarbon skeleton which is bound to carboxyl group by esterifying OH group on D ring with carboxyl group; R' represents a $C_1$-$C_3$ alkylene group; and X represent a halogen atom, amino group, hydroxyl group, carboxyl group or a salt thereof, with a modified or non-modified reactive group of an antitumor to form a binding group of $$-O-,\ -COO-,\ -CONH-,\ -NH-\ \text{or}\ -N-.$$

DETAILED DESCRIPTION OF THE PREFERRED EMBODIMENTS

The steroid hormone-antitumor derivatives of the present invention (hereinafter referring to antitumor derivative) are compounds obtained by binding a special steroid hormone (it selectively binds to special cells) to an antitumor drug (it destroy special cells). with a binding group. Therefore, the antitumor derivative of the present invention selectively feeds an antitumor drug with a carrier of a steroid hormone to steroid hormone receptive cells thereby destroying selectively special steroid hormone receptive organs and cells in body tissues.

The combinations of the special steroid hormones and the physiologically active material as an antitumor can be easily considered by persons skilled in the medical field.

The steroid hormone receptive cells are well-known. On the other hand, the relations of antitumor drugs and tumor or cancer cells are also well-known with many clinical data and pharmacological data.

The steroid hormones are preferably compounds having cyclopentanophenanthrene carbon skeleton and OH group on D ring especially steroids having cyclopentanophenanthrene carbon skeleton having up to 35 carbon atoms (including substituents) such as gonane, estrane or androstane hydrocarbon skeleton, and having OH group on D ring especially at 17-position.

Suitable substituents include alkyl groups such as methyl and ethyl group; halogen atoms such as chlorine, bromine and iodine atoms; ethynyl group, hydroxyl group, ketone group, acyl group such as acetoxy, propionyloxy group, alkoxyl group, benzoyloxy group or double bond in its skeleton. The substituent can be introduced in up to four positions especially 3-position. The isomers in the form of α,β-position are also included.

Suitable steroid hormones include
1,3,5(10)-estratriene-3,17β-diol(3,17β-estratriene);
1,3,5(10)-estratriene-3,17α-diol(3,17α-estratriene);
3,17β-dihydroxy-1,3,5(10)-estratriene-16-one(16-ketoestradiol);
1,3,5(10)-estratriene-3,16α,17β-triol(estratriol);
1,3,5(10)-estratriene-3,16β,17β-triol(16-epiestriol);
1,3,5(10)-estratriene-3,16α,17α-triol(17-epiestriol);
17β-hydroxy-1,3,5(10)-estratriene-3-acetate;
17β-hydroxy-1,3,5(10)-estratriene-3-propionate;
17β-hydroxy-1,3,5(10)-estratriene-3-benzoate;
17α-hydroxy-1,3,5(10)-estratriene-3-benzoate;
16α,17β-dihydroxy-1,3,5(10)-estratriene-3-benzoate;
16α-methyl-3-methoxy-1,3,5(10)-estratriene-16β,17β-diol;
17β-hydroxy-4-androsten-3-one(testosterone);
17β-hydroxy-17α-methyl-4-androsten-3-one(methylteststerone);
9α-fluoro-11β,17β-dihydroxy-17α-methyl-4-androsten-3-one(fluoxymesterone);
17β-hydroxy-17α-methyl-5β-androsten-3-one(oxandrostene);
17β-hydroxy-5α-androsten-3-one(androstanone); and
17β-hydroxy-17α-methyl-1,3,5(10)-estratriene-3-one(-methyl estrenone).

The derivatives of said steroid hormones whose OH group at 3-position is converted to an acyl group such as acetoxy, propionyloxy or benzoyloxy group are especially preferable. The conversion can be easily carried out by reacting OH group at 3-position of the steroid hormone with an acid halide.

The steroid hormone or its acylated derivative is converted to the derivative having the group of $$-O-\underset{\underset{O}{\|}}{C}-R'X$$

before binding to the antitumor drug. The position to which the group of $$-O-\underset{\underset{O}{\|}}{C}-R'X$$

is introduced must be selected to prevent the active position of the steroid hormone and it is on D ring in the steroid nomenclature.

The steroid hormone derivative can be obtained by reacting a binding agent with the steroid hormone or its derivative. The binding agent should not cause toxicity. The binding agent forming ester bond reacts with OH group on D ring of the steroid hormone.

The binding agent can be a compound having the formula $$X'(CH_2)_nCOOH$$

(n is 1 to 4; and X' is a halogen atom (Br, Cl) such as α-monochloroacetic acid, α-monobromoacetic acid, and β-monobromopropionic acid, monobromobutyric acid; a compound having the formula $$X'(CH_2)_nCOX''$$

(n is 1 to 4; X' is a halogen atom (Br, Cl); X'' is a halogen atom (Br, Cl) such as α-monochloroacetylchloride and α-monobromoacetylbromide; a compound having the formula $$OH(CH_2)_nCOOH \text{ or } HOOC(CH_2)_nCOOH$$

such as malonic acid, succinic acid, glutaric acid, adipic acid; glycolic acid, an acid halide thereof or an acid anhydride thereof; or a compound having the formula $$HN_2(CH_2)_nCOOH$$

such as α-aminoacetic acid and β-aminopropionic acid; or methyl succinate or methyl glutarate.

On the other hand, X group of the binding agent is reactive with the reactive group of the antitumor drug and X group should be selected to obtain easily the steroid hormone-antitumor derivatives. In the selection of X, a group which is highly reactive with the reactive group or its convertible group of the antitumor drug can be selected by a person skilled in the art.

It is also possible to react the binding agent with the antitumor drug and then to react the modified antitumor drug with OH group on D ring of the steroid hormone.

The present invention is to effectively transfer the antitumor drug to the tumor or cancer cells. The antitumor drugs can be selected from the known antitumor drugs.

Suitable antitumor drugs used in the present invention are described in certain classification.

(A) Alkylating agents:

(I) Nitrogen mustard type:

p-[bis(2-chloroethyl)amino]-L-phenylalanine;
5-bis(2-chloroethyl)amino-2,4-dioxo-pyrimidine, N,N-bis(2-chloroethyl)-N',O-propylene-phosphoric acid ester diamide;
tris(2'-chloroethyl)-aminohydrochloride;
N-(2-chloroethyl)-N'-(2-chloroethyl)-N',O-propylene-phosphoric acid ester diamide; and
4-hydroperoxy-isophosphamide.

(II) Ethyleneimines:

2,4,6-triethyleneimino-s-triazine;
N,N',N''-triethylene-thiophosphoramide;
2,3,5-tris-ethyleneimino-1,4-benzoquinone; and
2,5-bis(1-aziridinyl)-3-(2-carbamoyloxy-1-methoxyethyl)-6-methyl-1,4-benzoquinone.

(III) Nitrosoureas:

1,3-bis(2-chloroethyl)-1-nitrosourea;
1-(2-chloroethyl)-3-(4-methylcyclohexyl)-1-nitrosourea;
1-(4-amino-2-methylpyrimidin-5-yl)methyl-3-(2-chloroethyl)-3-nitrosourea hydrochloride;
2-(N'-methyl-N'-nitrosoureido)-2-deoxy-D-glucopyranoside;
methyl-2-[N'-(2-chloroethyl)-N'-nitrosoureido]-2-deoxy-D-glucopyranoside; and
1-(2-chloroethyl)-3-cyclohexcyl-1-nitrosourea.

(B) Antimetabolites:

4-aminopteroyl-glutamic acid;
4-amino-$N^{10}$-methylpteroyl-glutamic acid;
6-mercraptopurine;
6-mercaptopurineriboside;
2-amino-6-hydroxy-8-azapurine;
o-diazoacetyl-L-serine;
6-diazo-5-oxo-L-norleucine;
5-fluorouracil;
5-fluorouridine;
5-fluoro-2'-deoxyuridine;
1-(2'-tetrahydrofuryl)-5-fluorouracil;
cytosinearabinoside;
$N^4$-acyl-cytosinearabinoside;
2,2'-anhydro-1-β-arabinofuranocylcytosine hydrochloride;
methyl-1-(5-fluoro-1H-2-oxo-pyrimidin-4-yl)-β-D-glucopyranuronate; and
5-azacytidine.

(D) Antibiotics:

Mitomycine C,
Bleomycin $A_2$,
Daunorubicin, Doxorubicin,
Sarkomycin,
Rubidazone.

(D) Natural Product Antitumors:

Vincristine,
Vinblanstine,
Mytansine,
VP-16,

VM-26,

The following is the typical condition in the reactions.

The binding agent reacts with OH group on D ring of the steroid hormone in the presence or absence of a catalyst in a solvent such as carbon tetrachloride, chloroform, tetrahydrofuran, dimethylsulfoxide (DMSO), dimethylformamide (DMF), pyridine and acetone. The reaction temperature is usually ranging from −50° C. to 200° C. preferably −20° C. to 100° C. The reaction time is usually ranging from 0.5 to 48 hours preferably 1 to 24 hours.

The catalyst can be acids such as p-toluenesulfonic acid; and amines such as pyridine and triethylamine.

The antitumor drugs reacts with the reaction product in the presence or absence of a catalyst in a solvent such as DMSO, DMF, ether, pyridine, toluene, carbon tetrachloride, chloroform, tetrahydrofuran (THF).

The reaction temperature is usually ranging from −20° C. to 100° C. preferably −10° C. to 80° C. The reaction time is usually ranging from 2 to 100 hours.

The resulting product is purified to obtain the steroid hormone-antitumor derivative.

The catalyst can be triethylamine, $BF_3$ or acids such as paratoluenesulfonic acid.

The same compound can be also produced by reacting the binding agent with the antitumor drug and then, reacting the reaction product with OH group on D ring of the steroid hormone to form an ester bond.

The preparations of these products will be further understood by the following examples which show only certain embodiments and the conditions for the reactions can be modified.

The resulting steroid hormone-antitumor derivatives of the present invention are confirmed by the IR spectrum, mass spectrometry, the elementary analysis and the melting point, etc.

It was further confirmed by the tests for acute toxicity, binding function into tumor or cancer cells and antitumor effect, that the steroid hormone-antitumor derivatives of the present invention have remarkably low toxicity, excellent binding function into tumor or cancer cells and excellent antitumor effect.

The steroid hormone-antitumor derivatives of the present invention have remarkably lower toxicity in comparison with the known antitumor drugs. The reason is not realized at the present stage and should be studied further. It is considered that such effects will be supported by certain unknown mechanism beside the medical effect based on the usual concept of the receptor.

When the steroid hormone-antitumor derivatives of the present invention are used as therapeutic medicine, medical compositions for administration can be prepared by the conventional methods for the known antitumors.

The steroid hormone-antitumor derivatives of the present invention can be formulated in desirable forms for injection, oral administration, intravagina administration or coating. When they are formulated in solid forms for oral administration such as tablet, pill, granules, powder, capsule, it is possible to admix a binder, a diluting agent, a filler, a lubricant, a surfactant or a disintegrator in the formulation. When they are formulated in liquid forms for oral administration, the formulation can be an aqueous suspension, an oily suspension, a solution, a syrup and a shake mixture. When they are formulated in a form of suppository, the formulation can be prepared by using a hydrophobic or hydrophilic base and a stabilizer, a disintegrator, or a coloring agent. When they are formulated in a form of injection, an aqueous solution, a solubilizer, a nutrient, a stabilizer, a surfactant can be added. In order to maintain or to improve medical effect, a base, an acid or a salt can be incorporated as desired.

These compositions can be prepared by incorporating the active gradient at a ratio of 0.001–90% by weight preferably 0.01–60% by weight.

The formulated steroid hormone-antitumor derivatives of the present invention can be administrated by oral administration, percutaneous adsorption, intramuscular injection, intraperitoneal injection, intravenous injection, intrarectal injection, local administration and subcutaneous injection.

The dose of the steroid hormone-antitumor derivative of the present invention is ranging from about 0.01 to 50 mg/kg/day/(person) in the oral administration and it is ranging from about 0.001 to 20 mg/kg/day/(person) in the intravenous injection.

The steroid hormone-antitumor derivatives of the present invention have the following characteristics.

(1) When cancer is formed in a tissue having its receptor, the product selectively attacks the tumor or cancer cells of the tissue to destroy the tumor or cancer cells. Thus, it is effective by only small dosage.

(2) The product has lower side effect in comparison with those of the administration of the known antitumor drugs. Thus, it can be administered for a long period and accordingly, tumor or cancer cells can be completely destroyed.

(3) The steroid hormone used as the carrier component in the steroid hormone-antitumor derivative, has a single structural composition and its physiologic activity is clearly known. Thus, the product can be administrated without any anxiety.

(4) The structure, and activity of the antitumor component in the steroid hormone-antitumor derivative are already known. Thus, the product can be administrated without any anxiety.

(5) The receptor of the tumor or cancer cells can be analyzed. The corresponding steroid hormone or its derivative can be selected as a carrier component for the steroid hormone-antitumor derivative. The therapeutic for various cancers can be considered by selecting the carrier component.

(6) The steroid hormone-antitumor derivative can be administrated by the conventional form of the formulation such as oral administration, injection and suppository.

(7) The products of the present invention have excellent characteristics to highly contribute for human-being as well as medical development.

The products of the present invention are also effective as a stabilizer for high polymers especially polyolefins.

The present invention will be further illustrated by certain examples and references which are provided for purposes of illustration only and are not intended to be limiting the present invention.

EXAMPLE 1

(1-1) Preparation of 3-hydroxy-1,3,5(10)-estratriene-17β-monobromoacetate:

10 Grams of 1,3,5(10)-estratriene-3,17β-diol was dissolved in 400 ml. of anhydrous tetrahydrofuran (THF), and then 8.8 g. of pyridine was added.

A solution of 22.5 g. of monobromoacetylbromide in 74 g. of carbon tetrachloride was added dropwise to the resulting solution at about $-5°$ C. to $-7°$ C. The mixture was kept for one night. After the reaction, the resulting precipitate was separated by a filtration. The solvent was distilled off from the filtrate. The residue was dissolved in ether and recrystallized from ether to obtain 1,3,5(10)-estratriene-3,17β-bis(monobromoacetate). 2 Grams of the product was dissolved in 900 ml. of methanol and the solution was cooled to $-5°$ C. A solution of 0.24 g. of $K_2CO_3$ in 20 ml. of water was added dropwise to the resulting solution. After the reaction for 30 minutes, 1000 ml. of water was added and the resulting precipitate was separated and dried.

The result of elementary analysis, melting point and IR spectrum are as follows.

| Elementary analysis: | C | H | Br |
| --- | --- | --- | --- |
| Found (%) | 61.0 | 6.5 | 20.1 |
| Calculated (%) | 61.07 | 6.41 | 20.33 |

Melting point: 182°–183° C. IR spectrum: Table 2

(1-2) Preparation of 3-hydroxy-1,3,5(10)-estratriene-17β-monobromopropionate:

2.0 Grams of 1,3,5(10)-estratriene-3,17β-diol was dissolved in 50 ml. of anhydrous tetrahydrofuran and then 2 g. of paratoluenesulfonic acid monohydrate was added as a reaction catalyst and then 2.2490 g. of monobromopropionic acid was added and the mixture was refluxed at 80° C. for about 16 hours. After the reaction, the solvent was evaporated in vacuum at room temperature. The residue was added to water and washed three to four times with water (about 100 ml. in each time) to remove paratoluenesulfonic acid. The precipitate was separated by a filtration and dried in vacuum in a desiccator to obtain 2.42 g. of a crude product (yield 80.90%). The crude product was purified by a column chromatography with a mixed solvent of cyclohexane and ethyl acetate at a ratio of 50:30 by volume. The results of elementary analysis and melting point are as follows.

| Elementary analysis: | C | H | Br |
| --- | --- | --- | --- |
| Found (%) | 61.2 | 6.5 | 20.0 |
| Calculated (%) | 62.4 | 6.64 | 19.66 |

Melting point: 114°–117° C.

(1-3) Preparation of 3-hydroxy-1,3,5(10)-estratriene-17β-monochloropropionate:

2.0 Grams of 1,3,5(10)-estratriene-3,17β-diol was dissolved in 50 ml. of anhydrous tetrahydrofuran and then, 2.0 g. of paratoluenesulfonic acid monohydrate was added as a reaction catalyst and then 3 g. of monochloropropionic acid was added and the mixture was refluxed at 180° C. for about one night. After the reaction, the solvent was evaporated in vacuum at room temperature. The residue was added to water and washed three times with water (about 100 ml. in each time) to remove paratoluenesulfonic acid. The precipitate was separated by a filtration and dried in vacuum in a desiccator to obtain 2.5 g. of the crude product. The crude product was purified by a recrystallization from ethyl ether to obtain crystals.

The results of elementary analysis and melting point are as follows.

| Elementary analysis: | C | H | Cl |
| --- | --- | --- | --- |
| Found (%) | 68.5 | 7.5 | 9.5 |
| Calculated (%) | 69.5 | 7.45 | 9.79 |

Melting point: 120°–125° C.

(1-4) Preparation of 3-hydroxy-1,3,5(10)-estratriene-17β-monochloroacetate:

2.0 Grams of 1,3,5(10)-estratriene-3,17β-diol was dissolved in 50 ml. of anhydrous tetrahydrofuran and then 2.0 g. of paratoluenesulfonic acid monohydrate was added as a reaction catalyst and then 2.6 g. of monochloroacetic acid was added and the mixture was refluxed at 80° C. for 1 night. After the reaction, the solvent was evaporated in vacuum. The residue was washed three times with water (about 100 ml. in each time) to remove paratoluenesulfonic acid. The precipitate was separated by a filtration and dried in vacuum in a desiccator to obtain 2.5 g. of a crude product. The crude product was purified by a recrystallization from ethyl ether to obtain crystals.

The results of elementary analysis and melting point are as follows.

| Elementary analysis: | C | H | Cl |
| --- | --- | --- | --- |
| Found (%) | 68.0 | 7.0 | 10.0 |
| Calculated (%) | 68.87 | 7.17 | 10.19 |

Melting Point: 187°–190° C.

The following compounds were also prepared by the same process except using the corresponding starting compounds.

3-hydroxy-1,3,5(10)-estratriene-17α-monobromoacetate;

3-hydroxy-1,3,5(10)-estratriene-17α-monochloroacetate;

3-hydroxy-1,3,5(10)-estratriene-17α(β-monobromo)-propionate;

3-hydroxy-1,3,5(10)-estratriene-17β-(β-monochloro)-propionate;

3-hydroxy-1,3,5(10)-estratriene-17β-(γ-monobromo)butyrate;

3-hydroxy-1,3,5(10)-estratriene-17β-(γ-monochloro)butyrate;

3-hydroxy-1,3,5(10)-estratriene-17α-(γ-monochloro)butyrate;

3-hydroxy-1,3,5(10)-estratriene-17β-(δ-monobromo)valerate; and 3-hydroxy-1,3,5(10)-estratriene-17α-(δ-monochloro)valerate.

EXAMPLE 2

(2-1) Preparation of 3-acetoxy-1,3,5(10)-estratriene-17β-monobromoacetate:

10 Grams of 17β-hydroxy-1,3,5(10)-estratriene-3-acetate was dissolved in 400 ml. of anhydrous THF and then, 10 g. of pyridine was added.

A solution of 15 g. of monobromoacetylbromide in 75 g. of carbon tetrachloride was added dropwise to the resulting solution at about −5° C. to −7° C. The mixture was kept for one night. After the reaction, the resulting precipitate was separated by a filtration. The solvent was distilled off from the filtrate. The residue was dissolved in ether and recrystallized from ether to obtain 14 g. of 3-acetoxy-1,3,5(10)-estratriene-17β-monobromoacetate. The product was recrystallized.

The result of elementary analysis is as follows.

| Elementary analysis: | C | H | Br |
|---|---|---|---|
| Found (%) | 61.0 | 6.19 | 18.3 |
| Calculated (%) | 60.7 | 6.20 | 18.4 |

In the IR spectrum, the absorption band in 3600 to 3200 cm$^{-1}$ was not found.

The following compounds were also prepared by the same process except using the corresponding starting compounds.

3-acetoxy-1,3,5(10)-estratriene-17β-monochloroacetate;
3-acetoxy-1,3,5(10)-estratriene-17α-monochloroacetate;
3-acetoxy-1,3,5(10)-estratriene-17α-monobromoacetate;
3-acetoxy-1,3,5(10)-estratriene-17β-(β-monobromo)propionate;
3-acetoxy-1,3,5(10)-estratriene-17β-(β-monochloro)propionate;
3-acetoxy-1,3,5(10)-estratriene-17α-(β-monobromo)propionate;
3-acetoxy-1,3,5(10)-estratriene-17β-(γ-monobromo)butyrate;
3-acetoxy-1,3,5(10)-estratriene-17β-(γ-monochloro)butyrate;
3-acetoxy-1,3,5(10)-estratriene-17α-(γ-monobromo)butyrate;
3-acetoxy-1,3,5(10)-estratriene-17β-(δ-monobromo)valerate;
3-acetoxy-1,3,5(10)-estratriene-17β-(δ-monochloro)valerate;
3-acetoxy-1,3,5(10)-estratriene-17α-(δ-monobromo)valerate;
3-propionyloxy-1,3,5(10)-estratriene-17β-monobromoacetate;
3-propionyloxy-1,3,5(10)-estratriene-17α-monochloroacetate;
3-propionyloxy-1,3,5(10)-estratriene-17β-monochloroacetate;
3-propionyloxy-1,3,5(10)-estratriene-17β-(β-monobromo)propionate;
3-propionyloxy-1,3,5(10)-estratriene-17β-(β-monochloro)propionate;
3-propionyloxy-1,3,5(10)-estratriene-17β-(γ-monobromo)butyrate;
3-propionyloxy-1,3,5(10)-estratriene-17β-(δ-monobromo)valerate;
3-oxo-4-androstene-17β-monobromoacetate;
3-oxo-4-androstene-17β-monochloroacetate;
3-oxo-4-androstene-17β-(62-monobromo)propionate;
3-oxo-4-androstene-17β-(β-monochloro)propionate;
3-oxo-4-androstene-17β-(γ-monobromo)butyrate;
3-oxo-4-androstene-17β-(γ-monobromo)valerate;
17α-methyl-3-oxo-5β-androstene-17β-monobromoacetate;
17α-methyl-3-oxo-1,3,5(10)-estratriene-17β-monobromoacetate; and
17α-methyl-3-oxo-4-androstene-17β-monobromoacetate.

(2-2) Preparation of 3-benzoyloxy-1,3,5(10)-estratriene-17β-monobromoacetate:

10 Grams (3.67 mM) of 1,3,5(10)-estratriene-3,17β-diol was dissolved in 100 ml. of THF and 10 ml. of an aqueous solution containing 1.47 g. of NaOH was added. The mixture was stirred at about 30° C. to become a transparent solution. Then, the reaction mixture was concentrated and dried under a reduced pressure to vary syrup form to white crystals. In order to remove water, the crystals were dissolved in 100 ml. of methanol and dried under a reduced pressure on a water bath at 80° C. for 3 hours.

The resulting 3-sodium oxy-1,3,5(10)-estratriene-17β-ol was dissolved in 100 ml. of THF and 50 ml. of an ether solution containing 5.5 g. (39.1 mM) of benzoylochloride was added dropwise. The mixture was stirred at room temperature for 16 hours. After the reaction, the resulting sodium chloride was separated by the conventional method. The filtrate was evaporated to dryness. In order to decompose the unreacted benzoylchloride, 200 ml. of 0.1 N-NaOH aqueous solution was added. The mixture was stirred at room temperature. After 15 minutes, the resulting white crystals were separated by a filtration through a G-3 filter and washed with distilled water and dried and then they were recrystallized.

The product was analyzed by a thin layer chromatograph on a silica gel with a mixed development solvent (ethyl acetate and cyclohexane at a ratio of 50:30 by volume) to give the main spot of Rf: 0.34.

According to the tests of the elementary analysis, the melting point and the IR spectrum of the product, they were identical to those of the known data and accordingly, it was confirmed that the product is 17β-hydroxy-1,3,5(10)-estratriene-3-benzoate.

| Elementary analysis: | C | H |
|---|---|---|
| Found (%) | 79.1 | 7.6 |
| Calculated (%) | 79.68 | 7.44 |

Melting point: 190°–194° C. (known data 191°–196° C.) IR spectrum: Table 3.

In 100 ml. of THF, 7.0 g. (18.6 mM) and 2.0 g. (25.3 mM) of pyridine were dissolved and the mixture was cooled to about −5° C. A solution containing 15.5 g. of 30% monobromoacetylbromide-carbon tetrachloride in 50 ml. of THF was gradually added dropwise to the resulting mixture. After the addition, the mixture was stirred at −5° C. for 2 hours and then on an ice bath for hours, and kept in a refrigerator for 16 hours. After the reaction, the resulting white precipitate was separated through a G-4 filter and dried under a reduced pressure on a water bath at 30° C. and 200 ml. of ethyl ether was added and the mixture was stirred to obtain 5.3 g. of white crystals. The crude crystals were dissolved in 50 ml. of methanol at 30° C. and then, cooled to obtain 5.0 g. of white crystals.

The product was analyzed by a thin layer chromatography on a silica gel with a developer of a mixed solvent (ethyl acetate and cyclohexane at a ratio of 50:30 by volume) to give a single spot of Rf: 0.77.

The melting point of the product was 145° to 146° C.

The flow rate Rf of the product was different from the flow rate Rf: 0.34 of the starting compound of 17β-hydroxy-1,3,5(10)-estratriene-3-benzoate. In the IR spectrum, the absorption band in 3600–3200 cm$^{-1}$ was not found. It was confirmed that the product is 3-benzoyloxy-1,3,5(10)-estratriene-17β-monobromoacetate.

The following compounds were also prepared by the same process except using the corresponding starting compounds.

3-benzoyloxy-1,3,5(10)-estratriene-17α-monobromoacetate;

3-benzoyloxy-1,3,5(10)-estratriene-17β-monochloroacetate;

3-benzoyloxy-1,3,5(10)-estratriene-17β-monochloroacetate;

3-benxoyloxy-1,3,5(10)-estratriene-17β-(β-monobromo)propionate;

3-benzoyloxy-1,3,5(10)-estratriene-17β-(β-monochloro)propionate;

3-benzoyloxy-1,3,5(10)-estratriene-17β-(γ-monobromo)butyrate;

3-benzoyloxy-1,3,5(10)-estratriene-17β-(γ-monochloro)butyrate;

3-benzoyloxy-1,3,5(10)-estratriene-17β-(δ-monobromo)valerate; and 3-benzoyloxy-1,3,5(10)-estratriene-17β-(δ-monochloro)valerate.

EXAMPLE 3

Preparation of
3-acetoxy-1,3,5(10)-estratriene-17β-hemi-succinate

14 Grams of 17β-hydroxy-1,3,5(10)-estratriene-3-acetate, 15 g. of succinic anhydride and 140 ml. of anhydrous pyridine were mixed at room temperature and stirred for 18 hours to react them. The reaction mixture was poured on 1.5 liters of ice water and neutralized with 3 N-HCl and then it was diluted with water. The precipitated crystals were separated by washing with water and dried to obtain 16.5 g. of 3-acetoxy-1,3,5(10)-estratriene-17β-hemi-succinate.

In the IR spectrum of the recrystallized product, the absorption band in 3600–3200 cm$^{-1}$ was not found. The result of the elementary analysis of the product is as follows.

| Elementary analysis: | C | H |
| --- | --- | --- |
| Found (%) | 69.9 | 7.2 |
| Calculated (%) | 69.6 | 7.2 |

The following compounds were also prepared by the same process except using the corresponding starting compounds.

3-propionyloxy-1,3,5(10)-estratriene-17β-hemi-succinate;

3-benzoyloxy-1,3,5(10)-estratriene-17β-hemi-succinate;

3-oxo-4-androstene-17β-hemi-succinate;

3-oxo-5-androstane-17β-hemi-succinate; and 3-acetoxy-1,3,5(10)-estratriene-17β-hemi-maleate,

EXAMPLE 4

Preparation of
3-benzoyloxy-1,3,5(10)-estratriene-17β-monohydroxyacetate

In 50 ml. of anhydrous THF, 2 g. of 17β-hydroxy-1,3,5(10)-estratriene-3-benzoate was dissolved and 0.80 g. of glycollic acid was added and then, 1.8 g. of paratoluenesulfonic acid was further added. The mixture was refluxed on a water bath at 80° C. for 16 hours. After the reaction, the mixture was cooled and the unreacted paratoluenesulfonic acid and glycollic acid were separated by using 20 g. of a weak basic ion-exchange resin (Amberlite A-21) to obtain a pale yellow transparent solution. THF was distilled off under a reduced pressure to obtain 2.0 g. of white yellow crystals. The product was recrystallized from a mixed solvent of ethanol and ethyl ether(1:1) to obtain 1.5 g. of white crystals.

According to the elementary analysis and IR spectrum, it was confirmed that the product is 3-benzoyloxy-1,3,5(10)-estratriene-17β-monohydroxyacetate.

| Elementary analysis: | C | H |
| --- | --- | --- |
| Found (%) | 75.0 | 6.8 |
| Calculated (%) | 74.65 | 6.91 |

In the IR spectrum, the absorption bands at 1730 cm$^{-1}$ and 1230 cm$^{-1}$ were found and the fact shows the formation of the ester.

The following compounds were also prepared by the same process except using the corresponding starting compounds.

3-benzoyloxy-1,3,5(10)-estratriene-17γ-(monohydroxy)acetate;

3-benzoyloxy-1,3,5(10)-estratriene-17β-(β-monohydroxy)propionate;

3-benxoyloxy-1,3,5(10)-estratriene-17β-(γ-monohydroxy)butyrate;

3-acetoxy-1,3,5(10)-estratriene-17β-monohydroxyacetate;

3-propionyloxy-1,3,5(10)-estratriene-17β-monohydroxyacetate;

3-oxo-4-androstene-17β-monohydroxyacetate

17α-methyl-3-oxo-5β-androstane-17β-monohydroacetate;

17α-methyl-3-oxo-1,3,5(10)-estratriene-17β-monohydroxyacetate; and

17α-methyl-3-oxo-4-androstene-17β-monohydroxyacetate.

EXAMPLE 5

Preparation of
3-hydroxy-1,3,5(10)-estratriene-17β-[methyl-2-{N'-(2-chloroethyl)-α-N'-nitrosoureido}-2-deoxy-α-D-glucuronoyloxy]-acetate In 50 ml. of DMSO, 3.31 g. of 3-hydroxy-1,3,5(10)-estratriene-17β-monobromoacetate was dissolved, and then, 3.8 g. of silver methyl-N-benzyloxycarbonyl-α-D-glucosamineuronate was added to react them at room temperature for 3 days in the dark. The precipitate of AgBr was separated by a filtration through a G-4 filter for two times and then washed with acetone. The filtrate was concentrated at 70° C. to form syrup. Then, 100 ml. of distilled water was added to remove DMSO.

The mixture was cooled at 5° C. and was kept for 1 hour. The precipitate was separated by a filtration. The residue was washed with water and then, with petroleum ether and further with ethyl ether. The product was dried under a reduced pressure at room temperature to obtain 5.31 g. of a powdery product.

In 150 ml. of THF, 5.0 g. of the product was dissolved and the solution was charged in a 500 ml. autoclave and then, 5.0 g. of 10% Pd-carbon catalyst was added. The autoclave was purged with hydrogen gas. The mixture was stirred under feeding hydrogen to maintain 0.3 kg.cm² gauge for 64 hours.

It was confirmed that hydrogenation was accomplished by the elimination of the spot caused by the starting material in a silica gel thin layer plate. After the reaction, the catalyst was separated and washed with small amount of THF. The filtrate was concentrated and dried under a reduced pressure on a water bath. Petroleum ether was added to the product and the precipitated crystals were separated and dried. In order to remove water soluble impurities, the product was dispersed in water. The residual white yellow solid was separated and dried to obtain 3.8 g. of the product.

In a mixture of 150 ml. of acetonitrile and 20 ml. of water, 3.8 g. of the product was dispersed. The dispersion was stirred at room temperature for 30 minutes. The dispersion was admixed with 0.93 g. of 2-chloroethylisocyanate and the mixture was stirred at room temperature for 1 hour. After the reaction, isocyanate was eliminated and a transparent solution was obtained. The reaction mixture was concentrated under a reduced pressure at 30° C., and 100 ml. of water was added to the condensed mixture and stirred for 1 hour to form white crystals. The crystals were separated by a filtration and dried (yield: 92.8%) and purified by a silica gel chromatography with a mixed developer of 45 ml. of ethyl acetate, 45 ml. of cyclohexane and 10 ml. of ethanol to obtain a product having high purity (yield: 40%).

In a mixed solvent of 3.2 ml. of acetic acid and 6 ml. of ethanol, 200 mg. of the product was dissolved. $NaNO_2$ aqueous solution (4 ml. of water and 344 mg. of $NaNO_2$) was added dropwise to the resulting solution at 5° C. with stirring and the reaction was continued for 16 hours. After the reaction, the reaction mixture was concentrated under a reduced pressure to the volume of 2 ml. at 30° C. and then, 50 ml. of water was added to the concentrated product to precipitate yellowish red crystals. The crystals were separated by a filtration and dried (yield: 91%).

The product was purified by a silica gel chromatography with a mixed developer of ethyl acetate and cyclohexane (50:50 by volume). According to the elementary analysis, the IR spectrum and the melting point, it was confirmed that the product is the object compound.

| Elementary analysis: | C | H | N |
|---|---|---|---|
| Found (%) | 51.7 | 6.3 | 6.0 |
| Calculated (%) | 55.00 | 6.26 | 6.43 |

Melting point: 106°–120° C. (decomposed) IR spectrum: Table 4.

The following compounds were also prepared by the same process except using the corresponding starting compounds.

3-acetoxy-1,3,5(10)-estratriene-17β-[methyl-2-{N'-(2-chloroethyl)-N'-nitrosoureido}-2-deoxy-α-D-glucuronoyloxy]acetate;

3-propionyloxy-1,3,5(10)-estratriene-17β-[methyl-2-{N'-(2-chloroethyl)-N'-nitrosourecido}-2-deoxy-α-D-glucurononyloxy]acetate;

3-benzoyloxy-1,3,5(10)-estratriene-17β-[methyl-2-{N'(2-chloroethyl)-N'-nitrosoureido}-2-deoxy-α-D-glucuronoyloxy]acetate;

3-oxo-4-androstene-17β-[methyl-2-{N'-(2-chloroethyl)-N'-nitrosoureido}-2-deoxy-α-D-glucoronoyloxy]acetate;

3-hydroxy-1,3,5(10)-estratriene-17β-[methyl-2-{N'-(2-chloroethyl)-N'-nitrosoureido}-2-deoxy-α-D-glucuronoyloxy]acetate;

17α-methyl-3-oxo-5β-androstane-17β-[methyl-2-{N'-(2-chloroethyl)-N'-nitrosoureido}-2-deoxy-α-D-glucuronoyloxy]acetate;

17α-methyl-3-oxo-1,3,5(10)-estratriene-17β-[methyl-2-{N'-(2-chloroethyl)-N'-nitrosoureido}-2-deoxy-α-D-glucuronoyloxy]acetate; and 17α-methyl-3-oxo-4-androstene-17β-[methyl-2-{N'-(2-chloroethyl)-N'-nitrosoureido}-2-deoxy-α-D-glucuronoyloxy]acetate.

EXAMPLE 6

Preparation of
3-hydroxy-1,3,5(10)-estratriene-17β-[2-{N'-(2-chloroethyl)-N'-nitrosoureido}-2-deoxy-D-glucuronoyloxy]acetate In 70 ml. of DMSO, 3.465 g. of 3-hydroxy-1,3,5(10)-estratriene-17β-monobromoacetate was dissolved and 4.634 g. of silver benzyl-N-benzyloxycarbonyl-α-D-glucosamineuronate was added to the solution and the mixture was stirred at room temperature for 3 days to react them, in the dark. The precipitate of Ag Br was separated by a filtration through a G-4 filter for 2 times and washed with acetone. The filtrate was concentrated to the volume of 10 ml. at 70° C. Then, 100 ml. of distilled water was added to remove DMSO from the filtrate.

The reaction product was cooled at 5° C. and kept for 1 hour and the precipitate obtained was separated by a filtration and washed with water, with petroleum ether and then with ethyl ether and dried at room temperature under a reduced pressure to obtain 6.1 g. of a powdery product.

In 70 ml. of THF, 3.5 g. of the resulting compound was dissolved, and 3.5 g. of 10% Pd-carbon catalyst was added. Hydrogen gas was fed to the mixture at a rate of 15 ml./minute with vigorously stirring for 60 hours to react them. After the reaction, the catalyst was separated by a filtration through a G-4 filter and washed with a small amount of methanol. The filtrate was evaporated to dryness under a reduced pressure at room temperature. The residue was admixed with petroleum ether and the precipitate was separated and dried. In order to remove a water soluble impurity, the product was dispersed in water and the residual white yellow solid was separated and dried to obtain 2.0 g. of the compound.

In a mixed solvent of 30 ml. of acetonitrile and 2 ml. of water, 0.8 g. of the product was dissolved at 40° C. and the solution was cooled to 10° to 20° C. and 0.20 ml. of 2-chloroethylisocyanate was added and then the mixture was stirred for 60 minutes to react them. After the reaction, the reaction mixture was evaporated to dryness under a reduced pressure at 40° C. The residue was admixed with 50 ml. of water with stirring to obtain white precipitate. The precipitate was separated and washed with ether and with ethyl acetate and then, with water and dried under a reduced pressure. In 6 ml. of ethanol, 0.2 g. of the resulting product was dissolved and 3.2 ml. of acetic acid was added and the mixture was kept at 5° C. and then NaNO₂ aqueous solution (4 ml. of water; 344 mg. of NaNO₂) was added with stirring and the mixture was stirred for 18 hours to react them. After the reaction, the reaction mixture was concentrated under a reduced pressure and the residue was admixed with 50 ml. of water to form the precipitate. The precipitate was separated, washed with a small amount of water and dried under a reduced pressure at room temperature.

The product was purified by a silica gel chromatography with a developer of a mixed solvent of cyclohexane and acetic acid at a ratio of 50:50 by volume which was passed through a column of silica gel having more than 100 mesh at a rate of 0.172 cm./min.

According to the elementary analysis, the IR spectrum and the melting point, it was confirmed that the product is the object compound.

| Elementary analysis: | C | H | N | Cl |
|---|---|---|---|---|
| Found (%) | 53.9 | 5.9 | 6.5 | 5.5 |
| Calculated (%) | 54.33 | 6.09 | 6.56 | 5.54 |

Melting point: 110°–115° C. (decomposed) IR spectrum: Table 5.

The following compounds were also prepared by the same process except using the corresponding starting compounds.

3-acetoxy-1,3,5(10)-estratriene-17β-[2-{N'-(2-chloroethyl)-N'-nitrosoureido}-2-deoxy-D-glucuronoyloxy-]acetate;

3-propionyloxy-1,3,5(10)-estratriene-17β-[2-{N'-(2-chloroethyl)-N'-nitrosoureido}-2-deoxy-D-glucuronoyloxy]acetate;

3-benzoyloxy-1,3,5(10)-estratriene-17β-[2-{N'-(2-chloroethyl)-N'-nitrosoureido}-2-deoxy-D-glucuronoyloxy]acetate;

3-acetoxy-1,3,5(10)-estratriene-17β-[2-{N'-(2-chloroethyl)-N'-nitrosoureido}-2-deoxy-D-glucuronoyloxy]-propionate;

3-acetoxy-1,3,5(10)-estratriene-17β-[2-{N'-(2-chloroethyl)-N'-nitrosoureido}-2-deoxy-D-glucuronoyloxy]-butyrate;

3-acetoxy-1,3,5(10)-estratriene-17β-[2-{N'-(2-chloroethyl)-N'-nitrosoureido}-2-deoxy-D-glucuronoyloxy]-valerate;

3-oxo-4-androstene-17β-[2-{N'-(2-chloroethyl)-N'-nitrosoureido}-2-deoxy-D-glucuronoyloxy]acetate;

17α-methyl-3-oxo-5β-androstane-17β-[2-{N'-(2-chloroethyl)-N'-nitrosoureido}-2-deoxy-D-glucuronoyloxy]acetate;

17α-methyl-3-oxo-1,3,5(10)-estratriene-17β-[2-{N'-(2-chloroethyl)-N'-nitrosoureido}-2-deoxy-D-glucuronoyloxy]acetate; and 17α-methyl-3-oxo-4-androstene-17β-[2-{N'-(2-chloroethyl)-N'-nitrosoureido}-2-deoxy-D-glucuronoyloxy-]acetate.

EXAMPLE 7

Preparation of 3-hydroxy-1,3,5(10)-estratriene-17β-[2-(N'-methyl-N'-nitrosoureido)-2-deoxy-D-glucuronoyloxy]acetate In 70 ml. of DMSO, 13.465 g. of 3-hydroxy-1,3,5(10)-estratriene-17β-monobromoacetate was dissolved and then 4.634 g. of silver benzyloxy-N-benzyloxycarbonyl-D-glucosamineuronate was added to the solution to react them at room temperature for 3 days in the dark. The precipitate of AgBr was separated by a filtration through a G-4 filter for 2 times and washed with acetone. The filtrate was concentrated at 70° C. to the volume of 10 ml. and then 100 ml. of distilled water was added to remove DMSO from the filtrate. The solution was cooled at 5° C. and kept for 1 hour to form the precipitate. The precipitate was separated by a filtration and washed with water, with petroleum ether and then with ethyl ether and dried under a reduced pressure at room temperature to obtain 6.1 g. of the powdery product.

In 70 ml. of THF, 3.5 g. of the product was dissolved and then 3.5 g. of 10% Pd-carbon catalyst was added. Hydrogen gas was fed to the mixture at a rate of 15 ml./minute with vigorously stirring, for 60 hours to react them. After the reaction, the catalyst was separated by a filtration through a G-4 filter and washed with a small amount of methanol. The filtrate was evaporated to dryness under a reduced pressure at room temperature. The residue was admixed with petroleum ether and the precipitate was separated and dried. In order to remove a water soluble impurity, the product was dispersed in water and the residual white yellow solid was separated and dried to obtain 2.0 g. of the compound.

In a mixed solvent of 30 ml. of acetonitrile and 2 ml. of water, 0.8 g. of the product was dissolved at 40° C. and the solution was cooled to 10° to 20° C. and 0.16 ml. of methylisocyanate was added and then the mixture was stirred for 60 minutes to react them. After the reaction, the reaction mixture was evaporated to dryness under a reduced pressure at 40° C. The residue was admixed with 50 ml. of water with stirring to obtain white precipitate. The precipitate was separated and washed with ether and, with ethyl acetate and then washed with water and dried under a reduced pressure to obtain the product (melting point: 130°–137° C.).

In 6 ml. of ethanol, 0.2 g. of the resulting product was dissolved and 3.2 ml. of acetic acid was added and the mixture was kept at 5° C. and then NaNO₂ aqueous solution (4 ml. of water; 344 mg. of NaNO₂) was added with stirring and the mixture was stirred for 18 hours to react them. After the reaction, the reaction mixture was concentrated under a reduced pressure and the residue was admixed with 50 ml. of water to form the precipitate. The precipitate was separated by a filtration and washed with a small amount of water and dried under a reduced pressure at room temperature.

The product was purified by a silica gel chromatography with a developer of a mixed solvent of cyclohexane and acetic acid at a ratio of 50:50 by volume which was passed through a column of silica gel having more than 100 mesh at a rate of 0.172 cm./min.

According to the elementary analysis, the IR spectrum and the melting point, it was confirmed that the product is the object compound.

| Elementary analysis: | C | H | N |
|---|---|---|---|
| Found (%) | 57.3 | 6.3 | 6.9 |
| Calculated (%) | 56.9 | 6.1 | 7.1 |

Melting point: 109°–115° C. IR spectrum: Table 6.

The following compounds were also prepared by the same process except using the corresponding starting compounds.

3-acetoxy-1,3,5(10)-estratriene-17β-[2-(N'-methyl-N'-nitrosoureido)-2-deoxy-D-glucuronoyloxy]acetate;

3-propionyloxy-1,3,5(10)-estratriene-17β-[2-(N'-methyl-N'-nitrosoureido)-2-deoxy-D-glucuronoyloxy]acetate;

3-benzoyloxy-1,3,5(10)-estratriene-17β-[2-(N'-methyl-N'-nitrosoureido)-2-deoxy-D-glucuronoyloxy]acetate;

3-acetoxy-1,3,5(10)-estratriene-17β-[2-(N'-methyl-N'-nitrosoureido)-2-deoxy-D-glucuronoyloxy]propionate;

3-acetoxy-1,3,5(10)-estratriene-17β-[2-(N'-methyl-N'-nitrosoureido)-2-deoxy-D-glucuronoyloxy]butyrate;

3-acetoxy-1,3,5(10)-estratriene-17β-[2-N'-methyl-N'-nitrosoureido)-2-deoxy-D-glucuronoyloxy]valerate;

3-oxo-4-androstene-17β-[2-N'-methyl-N'-nitrosoureido)-2-deoxy-D-glucuronoyloxy]acetate;

17α-methyl-3-oxo-5β-androstane-17β-[2-N'-methyl-N'-nitrosoureido)-2-deoxy-D-glucuronoyloxy]acetate;

17α-methyl-3-oxo-1,3,5(10)-estratriene-17β-[2-N'-methyl-N'-nitrosoureido)-2-deoxy-D-glucuronoyloxy]acetate; and 17α-methyl-3-oxo-4-androstene-17β-[2-N'-methyl-N'-nitrosoureido)-2-deoxy-D-glucuronoyloxy]acetate.

EXAMPLE 8

(8-1) Preparation of 3-hydroxy-1,3,5(10)-estratriene-17β-[5-fluoro-2,4-dioxo-pyrimidin-1-yl]acetate In 5 ml. of distilled water, 100 mg. of 5-fluoro-2,4-dioxo-pyrimidin (5-Fu) was dispersed and then KOH aqueous solution (10 ml. of water; 50.8 mg. of KOH) was slowly added. After the addition, the mixture was stirred for 30 minutes to form a transparent solution having pH of 8 to 9 and then 2.6% aqueous solution of AgNO₃ was added dropwise and the mixture was stirred for 1 hour in the dark. The precipitate was separated by a filtration and washed with water and dried under a reduced pressure to obtain silver salt of 5-Fu (yield: 93.4%).

In 10 ml. of DMSO, 130 mg. of silver salt of 5-Fu and 215 mg. of 3-hydroxy-1,3,5(10)-estratriene-17β-monobromoacetate were added to react them for 2 days in the dark. The precipitate was separated by a filtration. The filtrate was concentrated under a reduced pressure and then water was added to precipitate the product. The precipitate was washed with water and dried. The product was purified by a silica gel chromatography with a mixed solvent of ethyl acetate and cyclohexane at a ratio of 50:50 by volume which was passed through a column of silica gel.

According to the elementary analysis, the IR spectrum and the melting point, it was confirmed that the product is the object compound. (yield: 89.4%)

| Elementary analysis: | C | H | N |
|---|---|---|---|
| Found (%) | 64.6 | 6.5 | 5.9 |
| Calculated (%) | 65.14 | 6.10 | 6.33 |

Melting point: 282°–236° C. (melt-decomposed) IR spectrum: Table 7.

(8-2) Preparation of 3-benzoyloxy-1,3,5(10)-estratriene-17β-[5-fluoro-2,4-dioxo-pyrimidin-1-yl]acetate 5.0 Grams of 3-benzoyloxy-1,3,5(10)-estratriene-17β-monobromoacetate was dissolved in 50 ml. of DMF, and the solution was added dropwise to a solution of 1.29 g. of 5-fluoro-2,4-dioxo-pyrimidin-1-yl (5-Fu) and 1.5 g of triethylamine in 50 ml. of DMF at room temperature to react them at room temperature for 24 hours. After the reaction, DMF was evaporated under a reduced pressure on a water bath at 50° C. The residue was admixed with water and the mixture was stirred at room temperature. As a result, white-yellow product was precipitated. The crystals were separated by a centrifugal separation and washed two times with the equal amount of water and then the crystals were collected by a centrifugal separator and dried under a reduced pressure. 100 ml. of ethanol was added and the ethanol soluble component was separated and dried under a reduced pressure to obtain 4.5 g. of white crystals.

The product was analyzed by a thin layer chromatography on a silica gel with a developer of a mixed solvent (ethyl acetate and cyclohexane at a ratio of 50:50 by volume) to give a main spot of Rf: 0.32.

The crude crystals were recrystallized from a mixed solvent of ethyl acetate and cyclohexane. The product was analyzed by a thin layer chromatography in the same condition to give a single spot of Rf: 0.32.

According to the elementary analysis, the melting point and the IR spectrum, it was confirmed that the product is the object compound.

| Elementary analysis: | C | H | N |
|---|---|---|---|
| Found (%) | 67.0 | 5.62 | 5.0 |
| Calculated (%) | 67.2 | 5.60 | 5.06 |

Melting point: 205°–208° C. IR spectrum: Table 8.

(8-3) Preparation of 3-propionyloxy-1,3,5(10)-estratriene-17β-[5-fluoro-2,4-dioxo-pyrimidin-1-yl]acetate 2.84 Grams of 3-propionyloxy-1,3,5(10)-estratriene-17β-monobromoacetate and 1.5 g. of silver salt of 5-Fu were dispersed in 50 ml. of DMSO to react them at room temperature for 48 hours in the dark. After the reaction, the resulting AgBr was separated by a filtration through a G-4 filter. The filtrate was evaporated to dryness on a water bath at 80° C. under a reduced pressure. The residue was admixed with 50 ml. of acetone and an insoluble matter was separated by a filtration through a G-4 filter. The filtrate was further evaporated to dryness under a reduced pressure.

The resulting syrup residue having high viscosity was admixed with 100 ml. of distilled water and the mixture was stirred for 1 hour to precipitate white crystals. The crystals were filtered through a G-4 filter and washed with distilled water to remove DMSO The resulting crystals were dried under a reduced pressure in a desiccator to obtain 3.0 g. of crude crystals. The crude crystals were dissolved in a mixed solvent of cyclohexane and ethyl acetate at a ratio of 50:50 by volume. The product was purified by a column chromatography with silica gel.

According to the elementary analysis, the melting point and the IR spectrum, it was confirmed that the product is the object compound.

| Elementary analysis: | C | H | N |
|---|---|---|---|
| Found (%) | 66.00 | 6.18 | 5.65 |
| Calculated (%) | 65.00 | 6.22 | 5.62 |

Melting point: 190°–198° C. IR spectrum: Table 9.

(8-4) Preparation of
3-acetoxy-1,3,5(10)-estratriene-17β-[5-fluoro-2,4-dioxo-pyrimidin-1-yl]acetate 2.8 Grams of 3-acetoxy-1,3,5(10)-estratriene-17β-monobromoacetate and 1.5 g. of silver salt of 5-Fu were dissolved in 50 ml. of DMSO to react them for 3 days in the dark. The reaction mixture was filtered through a G-4 filter to remove AgBr. The filtrate was evaporated to dryness under a reduced pressure on a water bath at 80° C. The residue was admixed with 50 ml. of acetone and the mixture was filtered through a G-4 filter to remove an insoluble matter. The filtrate was further evaporated to dryness under a reduced pressure. The residue was admixed with 100 ml. of distilled water with stirring for 2 hours to obtain white precipitate for 2 hours. The precipitate was recrystallized from a mixed solvent of ethyl acetate and ethyl ether. The recrystallization was repeated to obtain 2.4 g. of white crystals.

According to the elementary analysis and the melting point, it was confirmed that the product is the object compound.

| Elementary analysis: | C | H | N |
|---|---|---|---|
| Found (%) | 64.9 | 5.90 | 5.65 |
| Calculated (%) | 64.44 | 5.99 | 5.78 |

Melting point: 201°–204° C.

(8-5) Preparation of
3-acetoxy-1,3,5(10)-estratriene-17β-[5-fluoro-2,4-dioxo-pyrimidin-1-yl]acetate In 3 ml. of dimethylformamide, 100 mg. of 5-fluoro-2,4-dioxo-pyrimidine (5-Fu) was dissolved and then 85.6 mg. of triethylamine was added and the mixture was stirred at 5° C. for 30 minutes. A solution of 302 mg. of 3-hydroxy-1,3,5(10)-estratriene-17β-monobromoacetate in 3 ml. of dimethylformamide was added dropwise to the resulting mixture and the mixture was stirred at 5° C. for 1 hour and then at room temperature for 22 hours to react them.

After the reaction, the resulting organic salt was separated by a filtration. The filtrate was evaporated to dryness under a reduced pressure on a water bath at 80° C. White fine crystals were precipitated. The crystals were admixed with 20 ml. of distilled water and the mixture was stirred at room temperature for 1 hour and cooled. The resulting white crystals were separated by a filtration and dried under a reduced pressure in a desiccator to obtain 150 mg. of crystals. The resulting crystals were recrystallized from a mixed solvent of methyl alcohol and ether at a ratio of 1:1 to obtain 120 mg. of white crystals.

The product was analyzed by a thin layer chromatography on a silica gel with a mixed solvent of ethyl acetate and cyclohexane at a ratio of 50:50 by volume to give a single spot of Rf: 0.24, by a coloring method with sulfuric acid or with iodine.

The result of the elementary analysis and the melting point of the product are as follows.

| Elementary analysis: | C | H | N |
|---|---|---|---|
| Found (%) | 65.5 | 6.2 | 6.2 |
| Calculated (%) | 65.14 | 6.10 | 6.33 |

Melting point: 282°–286° C. (decomposed)

The resulting 3-hydroxy-1,3,5(10)-estratriene-17β-(2,4-dioxo-5-fluoropyrimidin-1-yl)acetate (350 mg.) was dissolved in 2 ml. of anhydrous pyridine and 2 ml. of acetic anhydride was added to it and the mixture was kept in a refrigerator for 16 hours to react them. After the reaction, the mixture was evaporated to dryness under a reduced pressure on a water bath at 30° C. The residue was admixed with distilled water and the mixture was stirred for 1 hour to precipitate white crystals. The crystals were separated by a filtration through a G-4 filter and washed with distilled water and dried under a reduced pressure in a desiccator to obtain 330 mg. of white crystals. The crystals were recrystallized from a mixed solvent of ethyl acetate and ethyl ether. The product was analyzed by a thin layer chromatography on a silica gel with a developer of a mixed solvent (ethyl acetate and cyclohexane at a ratio of 50:50 by volume) to give a single spot of Rf: 0.38.

According to the elementary analysis, the melting point and the IR spectrum, it was confirmed that the product was the object compound.

| Elementary analysis: | C | H | N |
|---|---|---|---|
| Found (%) | 64.10 | 5.92 | 5.49 |
| Calculated (%) | 64.44 | 5.99 | 5.78 |

Melting point: 200°–204° C. IR spectrum: Table 10.

(8-6) Preparation of
3-propionyloxy-1,3,5(10)-estratriene-17β-[5-fluoro-2,4-dioxo-pyrimidin-1-yl]acetate In 2.5 ml. of anhydrous pyridine, 350 mg. of 3-hydroxy-1,3,5(10)-estratriene-17β-[5-fluoro-2,4-dioxo-pyrimidin-1-yl]acetate was dissolved and then 3 ml. of propionic anhydride was added and the mixture was kept in a refrigerator for 2 days to react them. After the reaction, the mixture was evaporated to dryness under a reduced pressure on a water bath at 30° C. The residue was admixed with distilled water and the mixture was stirred for 2 hours to obtain white crystals. The crystals were separated by a filtration through a G-4 filter. The product was recrystallized from a mixed solvent of ethyl acetate and ethyl ether to obtain 2.9 g. of crystals.

The following compound process except using the corresponding starting compounds.
3-acetoxy-1,3,5(10)-estratriene-17β-[5-fluoro-2,3-dioxy-pyrimidin-1-yl]acetate;
3-propionyloxy-1,3,5(10)-estratriene-17β-[5-fluoro-2,4-dioxo-pyrimidin-1-yl]acetate;
3-benzoyloxy-1,3,5(10)-estratriene-17β-[5-fluoro-2,4-dioxo-pyrimidin-1-yl]acetate;
3-acetoxy-1,3,5(10)-estratriene-17β-[5-fluoro-2,4-dioxo-pyrimidin-1-yl]propionate;
3-acetoxy-1,3,5(10)-estratriene-17β-[5-fluoro-2,4-dioxy-pyrimidin-1-yl]butyrate;
3-acetoxy-1,3,5(10)-estratriene-17β-[5-fluoro-2,4-dioxo-pyrimidin-1-yl]valerate;

3-oxo-4-androstene-17β-[5-fluoro-2,4-dioxo-pyrimidin-1-yl]acetate;

17α-methyl-3-oxo-5β-androstane-17β-[5-fluoro-2,4-dioxo-pyrimidin-1-yl]acetate;

17α-methyl-3-oxo-1,3,5(10)-estratriene-17β-[5-fluoro-2,4-dioxo-pyrimidin-1-yl]acetate;

17α-methyl-3-oxo-1,3,5(10)-estratriene-17β-[5-fluoro-2,4-dioxo-pyrimidin-1-yl]acetate;

17α-methyl-3-oxo-4-androstene-17β-[5-fluoro-2,4-dioxo-pyrimidin-1-yl]acetate;

3-acetoxy-1,3,5(10)-estratriene-17β-[5-fluoro-uridin-3-yl]acetate;

3-acetoxy-1,3,5(10)-estratriene-17β-[5-fluoro-2-deoxyuridine-3-yl]acetate; and 3-acetoxy-1,3,5(10)-estratriene-17β-[1-(2-tetrahydrofuryl)-5-fluorouracil-3-yl]acetate.

EXAMPLE 9

Preparation of bis 3-hydroxy-1,3,5(10)-estratriene-17β-oxycarbonylmethyl-4-amino-N[10]-methylpteroylglutamate In 5 ml. of DMSO, 200 mg. of silver 4-amino-N[10]-methylpteroylglutamate was dissolved and then, 235 mg. of 3-hydroxy-1,3,5(10)-estratriene-17β-monobromoacetate was added and the mixture was stirred at room temperature for 2 days in the dark. After the reaction, the precipitate of AgBr was separated by a filtration through a G-4 filter. The filtrate was concentrated under a reduced pressure at 80° C. The resulting oily product was admixed with distilled water to form yellow precipitate. The mixture was stirred for 1 hour whereby DMSO was removed to the water phase. The precipitate was separated by a filtration through a G-4 filtrate. The precipitate was washed with distilled water and dried under a reduced pressure in a desiccator to obtain 258.5 mg. of the crude product (theoretical amount: 322.2 mg; yield of crude product; 80.23%).

In 25 ml. of THF, 200 mg. of the crude product was dissolved and then, 10 ml. of distilled water was added, and then, 1.2 g. of ion-exchange resin (Diaion WA-20: ion-exchange capacity of 25 meq./ml.: d 0.60 g./cc) (50×10$^{-4}$ mole) and the mixture was stirred at room temperature for about 1 hour. The pH of the solution was changed from 6~7 to 7~8. The ion-exchange resin was separated by a filtration through a G-4 filter. The filtrate was concentrated under a reduced pressure on a water bath to remove THF. The residue was dried by a freeze-drying (lyophilization) to obtain 200 mg. of yellow powdery product.

According to the IR spectrum, the elementary analysis, the ninhydrin reaction and the melting point, it was confirmed that the product is the object compound.

| Elementary analysis: | C | H | N |
|---|---|---|---|
| Found (%) | 66.2 | 6.5 | 9.8 |
| Calculated (%) | 66.75 | 6.49 | 10.38 |

Melting point: 183°–194° C.
IR spectrum: Table 11.

The following compounds were also prepared by the same process except using the corresponding starting compounds.

bis[3-hydroxy-1,3,5(10)-estratriene-17β-oxocarbonylmethyl]-4-aminopteroylglutamate;

bis[3-acetoxy-1,3,5(10)-estratriene-17β-oxocarbonylmethyl]-4-amino-N[10]-methylpteroylglutamate;

3-hydroxy-1,3,5(10)-estratriene-17β-(6-diazo-5-oxo-L-norleucyloxy)acetate; and 3-hydroxy-1,3,5(10)-estratriene-17β-(o-diazoacetyl-L-seryloxy)acetate.

EXAMPLE 10

Preparation of 3-glycoloyl-1,2,3,4,6,11-hexahydro-3,5,12-trihydroxy-10-methoxy-6,11-dioxo-1-naphthacenyl-3'-(3-hydroxy-1,3,5(10)-estratriene-17β-oxycarbonylmethyl)amino-2',3',6'-trideoxy-α-L-lyxo-hexapyranoside In 5 ml. of DMF, 100 mg. of 3-glycoloyl-1,2,3,4,6,11-hexahydro-3,5,12-trihydroxy-10-methoxy-6,11-dioxo-1-naphthacenyl 3'-amino-2',3',6'-trideoxy-α-L-lyxo-hexapyranoside was dissolved and then 600 mg. of 10% triethylamine-DMF solution was added to the solution cooled with ice. The mixture was stirred for 15 minutes and then, 1 g. of 10% 3-hydroxy-1,3,5(10)-estratriene-17β-monobromoacetate-DMF solution. The mixture was further stirred for 30 minutes, and then, 400 mg of 10% triethylamine-DMF solution was added and the mixture was stirred under cooling with ice for 6 hours and then, at room temperature for 24 hours to react them. The reaction system was dark red color and contained white precipitate. The white precipitate was separated by a filtration through a G-4 filter and washed with 200 ml of ethyl acetate. The filtrate was admixed with 200 ml of water and the pH was adjusted to 1-2 with conc. HCl. The mixture was stirred for 1 hour whereby the ethyl acetate phase was changed to a bright red transparent solution and the water phase was changed to a pale red transparent solution.

The ethyl acetate phase was separated. The water phase was admixed with 200 ml of ethyl acetate to extract further. The operation was repeated once again.

The ethyl acetate phases (600 ml) were collected and washed with 200 ml of distilled water for 3 times. The ethyl acetate phase was dehydrated over anhydrous sodium sulfate and evaporated to dryness under a reduced pressure on a water bath. The resulting crude crystals were dissolved in 10 ml of a mixed solvent of ethyl acetate, cyclohexane and ethanol at ratios of 40:40:20 by volumes. The product was purified by the CLC-3 type centrifugal chromatography (silica gel) with the mixed solvent, to obtain 23.1 mg. of the purified product.

According to the elementary analysis, the IR spectrum, the UV spectrum, and the melting point, it was confirmed that the product is the object compound.

| Elementary analysis: | C | H | N |
|---|---|---|---|
| Found (%) | 65.1 | 6.0 | 1.7 |
| Calculated (%) | 65.90 | 6.19 | 1.64 |

Melting point: 117°–120° C.
IR spectrum: Table 12.

EXAMPLE 11

Preparation of 3-glycoloyl-1,2,3,4,6,11-hexahydro-3,5,12-trihydroxy-10-methoxy-6,11-dioxo-1-naphthacenyl-3'-(3-benzoyloxy-1,3,5(10)-estratriene-17β-oxycarbonylmethyl)amino-2',3',6'-trideoxy-α-L-lyxo-hexapyranoside In 5 ml. of DMF, 100 mg. of 3-glycoloyl-1,2,3,4,6,11-hexahydro-3,5,12-trihydroxy-10-methoxy-6,11-dioxo-1-naphthacenyl-3'-amino-2',3',6'-trideoxy-α-L-lyxo-hexapyranoside was dissolved and then 600 mg. of 10% triethylamine-DMF solution was added dropwise to the solution. The mixture was stirred at room temperature for 15 minutes and 200 mg. of 10% triethylamine-DMF solution was added and the mixture was stirred at room temperature for 20 hours. During the reaction, white precipitate was formed. After the reaction, 300 ml. of distilled water and 400 ml. of ethyl acetate were added and pH of the mixture was adjusted to 3 with conc. $H_2SO_4$ and the mixture was stirred and the ethyl acetate phase was separated.

The water phase was admixed with 400 ml. of ethyl acetate to extract the product further. The operation was repeated again and the ethyl acetate phases were collected (1200 ml.) and washed two times with distilled water. The solution had pH of 6.5–7. The ethyl acetate phase was dehydrated over anhydrous sodium sulfate and evaporated to dryness on a water phase at 40° C. to obtain 108.7 mg. of dark red crystals.

The crystals were dissolved in 20 ml. of a mixed solvent of ethyl acetate and cyclohexane and ethyl alcohol at ratios of 45:45:20 by volume and were purified by a silica gel column chromatography to obtain a yield of 45.1 mg..

The product was analyzed by a thin layer chromatography on a silica gel with the same mixed solvent to give a single spot of Rf: 0.4. The elementary analysis, the melting point and the IR spectrum are as follows.

| Elementary analysis: | C | H | N |
|---|---|---|---|
| Found (%) | 67.9 | 6.0 | 1.5 |
| Calculated (%) | 67.5 | 5.9 | 1.5 |

Melting point: 130°–140° C.
IR spectrum: Table 13

EXAMPLE 12

Preparation of
3-glycoloyl-1,2,3,4,6,11-hexahydro-3,5,12-trihydroxy-10-methoxy-6,11-dioxo-1-naphthacenyl-3'-(3-acetoxy-1,3,5(10)-estratriene-17β-oxy-carbonylmethyl)amino-2',3',6'-trideoxy-α-L-lyxo-hexpyranoside In 5 ml. of DMF, 100 mg. of 3-glycoloyl-1,2,3,4,6,11-hexahydro-3,5,12-trihydroxy-10-methoxy-6,10-dioxo-1-naphthacenyl-3'-amino-2',3',6'-trideoxy-α-L-lyxo-hexapyranoside was dissolved and then 600 mg. of 10% triethylamine-DMF solution was added dropwise to the solution. The mixture was stirred at room temperature for 15 minutes and then 200 mg. of 50% 3-acetoxy-1,3,5(10)-estratriene-17β-monobromoacetate-DMF solution. The mixture was further stirred for 15 minutes and then 200 mg. of 10% triethylamine-DMF solution was added and the mixture was stirred at room temperature for 24 hours. After the reaction, 300 ml. of distilled water and 400 ml. of ethyl acetate were added and pH of the mixture was adjusted to about 3 with conc. HCl and the mixture was stirred. The ethyl acetate phase was separated and the water phase was extracted two times with 40 ml. of ethyl acetate and the ethyl acetate phases were collected (1200 ml.) and washed two times with 300 ml. of distilled water. The ethyl acetate phase was separated and dehydrated over anhydrous sodium sulfate and evaporated to dryness under a reduced pressure at 40° C. to obtain 120 mg. of dark red crystals.

The crude crystals were purified by a silica gel column chromatography with a mixed solvent of ethyl acetate, cyclohexane and ethyl alcohol at ratios of 45:45:20 by volume to obtain a yield of 55 mg. of the product.

The elementary analysis and the IR spectrum are as follows.

| Elementary analysis: | C | H | N |
|---|---|---|---|
| Found (%) | 64.0 | 6.0 | 1.6 |
| Calculated (%) | 65.6 | 6.1 | 1.6 |

IR spectrum: Table 14

EXAMPLE 13

Preparation of
3-glycoloyl-1,2,3,4,6,11-hexahydro-3,5,12-trihydroxy-10-methoxy-6,11-dioxo-1-naphthacenyl-3'-(3-propionyloxy-1,3,5(10)-estratriene-17β-oxycarbonylmethyl)amino-2',3',6'-trideoxy-α-L-lyxo-hexapyranoside In 5 ml. of DMF, 100 mg. of 3-glycoloyl-1,2,3,4,6,11-hexahydro-3,5,12-trihydroxy-10-methoxy-6,11-dioxo-1-naphthacenyl 3'-amino-2',3',6'-trideoxy-α-L-lyxo-hexapyranoside was dissolved and 600 mg. of 10% triethylamine-DMF solution was added dropwise. The mixture was stirred at room temperature for 15 minutes and then 220 mg. of 50% 3-propionyloxy-1,3,5(10)-estratriene-17β-monobromoacetate-DMF solution was added and then the mixture was stirred at room temperature for 16 hours. After the reaction, 300 ml. of distilled water was added and pH of the mixture was adjusted to about 3. The product was extracted three times with 400 ml. of ethyl acetate. The ethyl acetate phase (1200 ml.) was washed two times with distilled water. The ethyl acetate phase was separated and dehydrated over anhydrous sodium sulfate and dried at 40° C. under a reduced pressure to obtain 130 mg. of dark red crystals.

The crude crystals were purified by a silica gel column chromatography with a mixed solvent of ethyl acetate, cyclohexane and ethyl alcohol at ratios of 45:45:20 by volume to obtain 50 mg. of the product.

The elementary analysis and the IR spectrum are as follows.

| Elementary analysis: | C | H | N |
|---|---|---|---|
| Found (%) | 65.0 | 6.1 | 1.5 |
| Calculated (%) | 65.9 | 6.3 | 1.5 |

IR spectrum: Table 15

The following compounds were also prepared by the same process except using the corresponding starting compounds.

3-glycoloyl-1,2,3,4,6,11-hexahydro-3,5,12-trihydroxy-10-methoxy-6,11-dioxo-1-naphthacenyl-3'-(3-butyloxy-1,3,5(10)-estratriene-17β-oxycarbonylmethyl)amino-2',3',6'-trideoxy-α-L-lyxo-hexapyranoside.

EXAMPLE 14

Preparation of
3-acetyl-1,2,3,4,6,11-hexahydro-3,5,12-trihydroxy-10-methoxy-6,11-dioxo-1-naphthacenyl-3'-(3-acetoxy-1,3,5(10)-estratriene-17β-oxycarbonylmethyl)amino-2',3',6'-trideoxy-α-L-lyxo-hexapyranoside In 2 g. of DMSO, 50 mg. (88.65 μ mole) of 3-acetyl-1,2,3,4,6,11-hexahydro-3,5,12-trihydroxy-10-methoxy-6,11-dioxo-1-naphthacenyl-3'-amino-2',3',6'-trideoxy-α-L-lyxo-hexapyranoside was dissolved and 98.7 mg. (99.67 μ mole) of 10.02% triethylamine-DMF solution was added. The mixture was stirred for 1 hour under cooling with ice and then 400 mg. (101.52 μ mole) of 9.98% estradiol-17β-monobromoacetate-DMF solution was added. The mixture was stirred for 30 minutes and 400 mg. (396.05 μ mole) of 10.02% triethylamine-DMF solution was divided into four portions and added them each 10 minutes. The mixture was stirred for 1 hour under cooling with ice and then the mixture was stirred at room temperature. After 1 hour, the precipitation was started. The mixture was stirred at room temperature for 48 hours. After the reaction, a water insoluble material was separated by a filtration through a G-4 filter and 200 ml. of water was added to the filtrate and pH of the solution was adjusted to 1 with 0.1 N-HCl. The product was extracted three times with 150 ml. of ethyl acetate and the extracted solution was washed two times with 100 ml. of water and dehydrated over anhydrous sodium sulfate. The extracted solution was evaporated to dryness under a reduced pressure to obtain 54.1 mg. of dark red solid product.

The product was dissolved in 4 ml. of a mixed solvent of cyclohexane, ethyl acetate and ethanol at ratios of 45:45:10 by volumes. The product was purified by the CLC-3 type centrifugal chromatography (silica gel) with the mixed solvent to obtain 18.9 mg. of the purified product.

According to the elementary analysis, the IR spectrum and the melting point, it was confirmed that the product is the object compound.

| Elementary analysis: | C | H | N |
|---|---|---|---|
| Found (%) | 66.9 | 6.31 | 1.70 |
| Calculated (%) | 67.2 | 6.36 | 1.67 |

Melting point: 145°–150° C.
IR spectrum: Table 16

The following compounds were also prepared by the same process except using the corresponding starting compounds.

3-acetyl-1,2,3,4,6,11-hexahydro-3,5,12-trihydroxy-10-methoxy-6,11-dioxo-1-naphthacenyl-3'-[3-propionyloxy-1,3,5(10)-estratriene-17β-oxycarbonylmethyl]amino-2',3',6'-trideoxy-α-L-lyxo-hexapyranoside; and 3-acetyl-1,2,3,4,6,11-hexahydro-3,5,12-trihydroxy-10-methoxy-6,11-dioxo-1-naphthacenyl-3'-[3-benzoyloxy-1,3,5(10)-estratriene-17β-oxycarbonylmethyl]amino-2',3',6'-trideoxy-α-L-lyxo-hexapyranoside.

EXAMPLE 15

Preparation of
2,4-bis(ethyleneimino)-6-(3-benzoyloxy-1,3,5,(10)-estratriene-17β-oxycarbonylmethyloxyethyl)amino-s-triazine In 50 ml of THF, 5 g of 3-benzoyloxy-1,3,5(10)-triene-17β-monohydroxacetate was dissolved and the mixture was cooled at −5° C., and then, 10 ml of a solution containing 13.3 mM of BF₃ in ethyl ether was gradually added. A solution containing 1.36 g of 2,4,6triethyleneimino-s-triazine in 5 ml of THF was gradually added to the resulting solution and the mixture was stirred at −5° C. for 2 hours, and then, at 18° C. on a water bath for 4 hours. After the reaction, 0.01 N-NaOH aqueous solution was gradually added to the reaction mixture to gradually decompose BF₃ and to adjust pH of the solution to 8–9. The reaction mixture was concentrated and dried under a reduced pressure on a water bath to obtain a yellow solid. The solid product was repeatedly extracted with a mixed solent of 200 ml of ethyl acetate and 100 ml of water. The operation was repeated. The reaction mixture was concentrated and dried under a reduced pressure on a water bath by removing ethyl acetate, to obtain 6.0 g of crude crystals.

The product was purified to remove the residual 3-benzoyloxy-1,3,5(10)-estratriene-17β-monohydroxyacetate by a column chromatography (silica gel) with a developer of a mixed solvent of water and n-propanol at a ratio of 35:65 by volume.

The elementary analysis, the IR spectrum and the molecular weight measurement were carried out. The result is as follows.

Molecular weight: 645: method of elevation of boiling point (nitrobenzene) (theoretical MW 637)

| Elementary analysis: | C | H | N |
|---|---|---|---|
| Found (%) | 65.9 | 6.0 | 14.0 |
| Calculated (%) | 67.71 | 6.58 | 13.17 |

IR spectrum: The absorption band at 3080 cm⁻¹ (C-H stretching vibration of aziridinyl ring) was found.

It was confirmed that the product was the object compound.

The following compounds were also prepared by the same process except using the corresponding starting compounds.

2,3-bis(ethyleneimini)-5-(3-benzoyloxy-1,3,5(10)-estratriene-17β-oxycarbonylmethyloxyethyl)amino-1,4-benzoquinone:

N,N'-bis(ethyleneimino)-N'-(3-benzoyloxy-1,3,5(10)-estratriene-17β-oxycarbonylmethyloxyethyl)amino-thiophosphosphamide; and 2-(ethyleneimino)-3-(2-carbamoyloxy-1-methoxyethyl)-6-methyl- 5-(3-benzoyloxy-1,3,5(10)-estratriene-17β-oxycarbonylmethyloxyethyl)amino-1,4-benzoquinone.

EXAMPLE 16

| COMPOSITION: | |
|---|---|
| Formula 1: | |
| Active ingredient | 50 wt. parts |
| Mannitol | 35 wt. parts |
| Sorbitol | 25 wt. parts |

-continued

COMPOSITION:

Formula 1:

| | |
|---|---|
| Carboxymethyl cellulose | 5 wt. parts |
| Magnesium stearate | 5 wt. parts |
| Talc | 40 wt. parts |

The components were mixed and pulverized and compressed to form a tablet having a diameter of 10 mm.

Formula 2:

| | |
|---|---|
| Active ingredient | 100 wt. parts |
| Lactose | 500 wt. parts |
| Sugar fatty acid ester | 10 wt. parts |
| Starch | 100 wt. parts |
| Water (1% sodium carboxy-methyl cellulose) | 100 wt. parts |

The components were kneaded and extruded through a pelleter in a form of granule and then dried and sieved to remain the particles ranging from 10 to 24 mesh to prepare granules for oral administration.

Formula 3:

The granules of Formula 2 were filed in a commercially available capsule to prepare 0.5 cc capsule.

Formula 4:

| | |
|---|---|
| Active ingredient | 0.2 wt. part |
| Nonionic surfactant | 3.0 wt. part |
| Physiological sodium chloride | 96.8 wt. part |

The components were mixed with heating and sterilized to prepare an injection.

TEST 1:

Acute toxicities and antitumor activities (in vivo)

(1) Acute toxicity ($LD_{50}$)

In the measurement of $LD_{50}$, eight ICR-JCL female mice (5 week age) were used as one group to breed in a transparent polycage, and each drug was dissolved in olive oil and administrated by routes of intraperitoneal injection (i.p.), oral administration (p.o.) and subcutaneous injection (s.c.), to the mice at one dose and then, their value of $LD_{50}$ by Litchfield-Wilcoxon graph method is obtained after 7 days. The results are shown in Table 18.

(2) Binding function to estrogen sensitive cells

Binding function of the active ingredients to estrogen sensitive cells.

The binding function of the active ingredient to tumor cells was tested by the method described in Biochemical Experiment text Hormone (I) (Nippon Seikagaku) (Tokyo Kagakudojin page 217-252, April 25, 1977).

Estradiol labelled by tritium ($^3H$) was incubated with uterus of rabbit to bind it and then, the sample was added to the system to measure the amount of free $^3H$-estradiol which was replaced by the added estradiol. The results are shown as the binding $^3H$-estradiol(%) in the cases adding 0.10 or 100 nM of the sample.

The smaller value shows higher binding into the estrogen sensitive cells.

(3) Antitumor Test (in vivo)

Pieces of human breast cancer cells having steroid hormone receptor was subcutaneously implanted under the arm of mice (BALB/C-nu/nu) (5 week age) to form solid tumors. After the solid tumors were established, each dispersion or solution of the active ingredient in olive oil was administered by oral dose or intraperitoneal injection each other day for 10 times or every days for 20 times. Twenty five days from the initial administration, the tumors were excised. Efficiency of inhibition of tumor proliferation was measured from (A) each average weight of excised tumors for 10 mice (the active ingredient was administrated) and (B) each average weight of excised tumors for 10 control mice.

$$\text{Inhibitory effect of tumor (\%)} = \left(1 - \frac{A}{B}\right) \times 100$$

The tests (1), (2), (3) for various active ingredients were carried out. The results are shown in Table 1.

In the acute toxicity tests, the toxicity of the antitumor derivative of the invention is remarkably lower than the corresponding antitumor itself. The toxicity of the antitumor derivative having acylated estradiol group instead of hydroxyl group at 3-position is further lower than the corresponding one.

IR spectrum

Table 2 IR bands ($cm^{-1}$)
  3460, 2920, 1725, 1615, 1580, 1494, 1395, 1297, 1286, 1245, 1225, 1182, 1148, 1130, 994, 960, 918, 872, 812, 782

Table 3 IR bands ($cm^{-1}$)
  3550, 1724, 1595, 1579, 1492, 1445, 1260, 1215, 1210, 1060, 698

Table 4 IR bands ($cm^{-1}$)
  3460, 3380, 2960, 2930, 2850, 1750, 1735, 1630, 1571, 1530, 1482, 1430, 1305, 1267, 1180, 1080, 965, 900, 870, 795, 760

Table 5 IR bands ($cm^{-1}$)
  3460, 3380, 2960, 2930, 2850, 1750, 1735, 1630, 1530, 1482, 1430, 1305, 1267, 1180, 1080, 1050, 1010, 965, 900, 870, 795, 760

Table 6 IR bands ($cm^{-1}$)
  3400, 2930, 1750, 1737, 1625, 1575, 1525, 1492, 1482, 1480, 1300, 1260, 1220, 1170, 1080, 1050, 970, 760

Table 7 IR bands ($cm^{-1}$)
  3320, 3060, 2920, 2860, 1745, 1725, 1690, 1670, 1610, 1580, 1500, 1445, 1420, 1380, 1284, 1245, 1210, 1134, 1000, 975, 919, 870, 817, 785, 690, 670

Table 8 IR bands ($cm^{-1}$)
  3400, 3180, 3060, 2910, 2860, 1748, 1728, 1700, 1685, 1660, 1595, 1578, 1487, 1446, 1415, 1377, 1338, 1259, 1240, 1205, 1168, 1142, 1054, 1018, 995, 969, 890, 786, 772, 709, 702

Table 9 IR bands ($cm^{-1}$)
  3400, 3201, 3060, 2920, 1742, 1720, 1695, 1608, 1587, 1489, 1465, 1431, 1410, 1378, 1340, 1240, 1205, 1170, 1145, 998, 893, 785

Table 10 IR bands ($cm^{-1}$)
  3400, 3200, 3060, 2920, 1742, 1720, 1695, 1608, 1587, 1489, 1465, 1430, 1410, 1378, 1340, 1240, 1205, 1170, 1145, 998, 893, 785

Table 11 IR bands ($cm^{-1}$)

3350, 2920, 1735, 1600, 1505, 1440, 1280, 1200

Table 12 IR bands (cm$^{-1}$)
3400, 2940, 2910, 2840, 1720, 1610, 1575, 1440, 1410, 1280, 1255, 1200, 1075, 1010, 800

Table 13 IR bands (cm$^{-1}$)
3420, 2940, 2915, 2860, 1730, 1720, 1615, 1578, 1490, 1440, 1410, 1375, 1280, 1260, 1208, 1100, 1080, 1060, 1018, 795, 705

Table 14 IR bands (cm$^{-1}$)
3400, 2940, 2910, 2840, 1740, 1720, 1615, 1575, 1490, 1440, 1410, 1375, 1345, 1280, 1255, 1225, 1200, 1110, 1075, 1010, 985, 950, 865, 800, 755

Table 15 IR bands (cm$^{-1}$)
3400, 2940, 2910, 2840, 1740, 1725, 1615, 1575, 1490, 1440, 1410, 1375, 1345, 1280, 1255, 1225, 1200, 1110, 1080, 1010, 985, 950, 865, 805, 750

Table 16 IR bands (cm$^{-1}$)
3430, 2920, 2850, 1735, 1725, 1660, 1617, 1580, 1500, 1445, 1380, 1285, 1260, 1230, 1120, 988, 950, 815, 790

TABLE 17

| | Binding $^3$H—estradiol | | |
|---|---|---|---|
| Test No. | 0 % | 10(nM) % | 100(nM) % |
| 1 | 54 | 36 | 16 |
| 2 | 54 | 45 | 30 |
| 3 | 54 | 55 | 55 |
| 4 | 55 | 56 | 56 |
| 5 | 55 | 37 | 17 |
| 6 | 54 | 28 | 16 |
| 7 | 54 | 36 | 25 |
| 8 | 54 | 55 | 53 |
| 9 | 56 | 35 | 19 |

| Test No. | Compounds used in tests in Table 17 |
|---|---|
| 1 | 1,3,5(10)-estratriene-3,17β-diol; |
| 2 | 3-hydroxy-1,3,5(10)-estratriene-17β-[methyl-2-{N'—(2-chloroethyl)-N'—nitrosoureido}-2-deoxy-α-D-glycuronoyloxy]-acetate; |
| 3 | methyl-2-N'—(2-chloroethyl)-N'—nitrosoureido-2-deoxy-α-D-glucopyranoside; |
| 4 | 3-acetyl-1,2,3,4,6,11-hexahydro-3,5,12-trihydroxy-10-methoxy-6,11-dioxo-1-naphthacenyl-3'-amino-2',3',6'-trideoxy-α-L-lyxo-hexapyranoside; |
| 5 | 3-acetyl-1,2,3,4,6,11-hexahydro-3,5,12-trihydroxy-10-methoxy-6,11-dioxo-1-naphthacenyl-3'-[3-hydroxy-1,3,5(10)-estratriene-17β-oxycarbonylmethyl]amino-2',3',6'-trideoxy-α-L-lyxo-hexapyranoside; |
| 6 | 3-hydroxy-1,3,5(10)-estratriene-17β-[2-(N'—methyl-N'—nitrosoureido)-2-deoxy-D-glucuronoyloxy]acetate; |
| 7 | 3-hydroxy-1,3,5(10)-estratriene-17β-[5-fluoro-2,4-dioxo-pyrimidin-1-yl]acetate; |
| 8 | 5-fluoro-2,4-dioxo-pyrimidine; |
| 9 | bis-[3-hydroxy-1,3,5(10)-estratriene-17β-oxycarbonylmethyl]-4-amino-N$^{10}$—methylpteroylglutamate. |

TABLE 18

| | Acute toxicity LD$_{50}$ | | Inhibitory effect of tumor (%) | | | |
|---|---|---|---|---|---|---|
| | | | i.p. | | p.o. | |
| Test No. | i.p. (mg/kg) | p.o. (mg/kg) | dose (mg/kg) | efficiency (%) | dose (mg/kg) | efficiency (%) |
| 1 | 48 | 210 | 3 | 18 | 10 | 13 |
| | | | 10 | 58 | 40 | 60 |
| 2 | 180< | 1000< | 1 | 90 | 10 | 73 |
| | | | 3 | 92 | 40 | 89 |
| 3 | 180< | 1000< | 1 | 90 | 10 | 79 |
| | | | 3 | 92 | 40 | 82 |
| 4 | 660< | 1000< | 5 | 92 | 10 | 77 |
| | | | 10 | 97 | 40 | 84 |

TABLE 18-continued

| | Acute toxicity LD$_{50}$ | | Inhibitory effect of tumor (%) | | | |
|---|---|---|---|---|---|---|
| | | | i.p. | | p.o. | |
| Test No. | i.p. (mg/kg) | p.o. (mg/kg) | dose (mg/kg) | efficiency (%) | dose (mg/kg) | efficiency (%) |
| 5 | 264 | 1000< | 10 | 20 | 10 | 69 |
| | | | 50 | 63 | 40 | 86 |
| 6 | 242 | 900 | 10 | 30 | 15 | 30 |
| | | | 20 | 50 | 30 | 60 |
| 7 | 605< | 2000< | 10 | 90 | | |
| | | | 20 | 100 | | |
| 8 | 680 | 3000< | 15 | 83 | 15 | 70 |
| | | | 30 | 90 | 30 | 81 |
| 9 | 800 | 3000< | 15 | 84 | 15 | 72 |
| | | | 30 | 93 | 30 | 87 |
| 10 | 740 | 3000< | 15 | 81 | 15 | 72 |
| | | | 30 | 91 | 30 | 83 |
| 11 | 235< | 3000< | 5 | 98 | 10 | 80 |
| | | | | | 50 | 93 |
| 12 | 94 | 230 | 5 | 48 | 10 | 31 |
| | | | 20 | 65 | 50 | 42 |
| 13 | | 730 | 10 | 20 | 10 | 20 |
| 14 | | 3000< | | | 10 | 63 |
| | | | | | 50 | 71 |
| 15 | | 3000< | | | 10 | 53 |
| | | | | | 50 | 79 |
| 16 | | 3000< | | | 10 | 69 |
| | | | | | 50 | 83 |
| 17 | | 3000< | | | 10 | 70 |
| | | | | | 50 | 79 |
| 18 | 5 | 20 | 0.5 | 47 | 1 | 59 |
| | | | 1 | 78 | | |
| 19 | 15< | 2000< | 0.1 | 90 | 1 | 72 |
| | | | 0.5 | 99 | 5 | 85 |
| 20 | 15< | 2000< | 0.1 | 74 | 1 | 78 |
| | | | | | 5 | 87 |
| 21 | 6.2 | 15.9 | 0.1 | 51 | 1 | 61 |
| | | | 0.5 | 57 | 3 | 72 |
| 22 | 100< | 1000< | 0.1 | 70 | 1 | 85 |
| | | | 0.5 | 80 | 3 | 90 |

| Test No. | Compounds used in tests in Table 18 |
|---|---|
| 1 | 2-[N'—-(2-chloroethyl-N'—nitrosoureido]-2-deoxy-D-glucopyranoside; |
| 2 | 3-hydroxy-1,3,5(10)-estratriene-17β-{2-[N'—(2-chloroethyl)-N'—nitrosoureido]-2-deoxy-D-glucuronoyloxy}acetate; |
| 3 | 3-hydroxy-1,3,5(10)-estratriene-17β-{methyl 2-[N'—(2-chloroethyl)-N'—nitrosoureido]-2-deoxy-α-D-glucuronoyloxy}acetate; |
| 4 | 3-hydroxy-1,3,5(10)-estratriene-17β-[2-(N'—methyl-N'—nitrosoureido)-2-deoxy-D-glucuronoyloxy]acetate; |
| 5 | 2-(N'—methyl-N'—nitrosoureido)-2-deoxy-D-glucopyranoside; |
| 6 | 5-fluoro-2,4-dioxo-pyrimidine; |
| 7 | 3-hydroxy-1,3,5(10)-estratriene-17β-[5-fluoro-2,4-dioxo-1-pyrimidin-1-yl]acetate; |
| 8 | 3-benzoyloxy-1,3,5(10)-estratriene-17β-[5-fluoro-2,4-dioxo-1-pyrimidin-1-yl]acetate; |
| 9 | 3-acetoxy-1,3,5(10)-estratriene-17β-[5-fluoro-2,4-dioxo-1-pyrimidin-1-yl]acetate; |
| 10 | 3-propionyloxy-1,3,5(10)-estratriene-17β-[5-fluoro-2,4-dioxo-pyrimidin-1-yl]acetate; |
| 11 | bis-[3-hydroxy-1,3,5(10)-estratriene-17β-oxycarbonylmethyl]-4-amino-N$^{10}$—methyl pteroyl glutamate; |
| 12 | 4-amino-N$^{10}$—methylpteroyl glutamate; |
| 13 | 3-glycoloyl-1,2,3,4,6,11-hexahydro-3,5,12-trihydroxy-10-methoxy-6,11-dioxo-1-naphthacenyl-3'-amino-2',3',6'-trideoxy-α-L-lyxo-hexapyranoside; |
| 14 | 3-glycoloyl-1,2,3,4,6,11-hexahydro-3,5,12-trihydroxy-10-methoxy-6,11-dioxo-1-naphthacenyl-3'-[3-hydroxy-1,3,5(10)-estratriene-17β-oxycarbonylmethyl]amino-2',3',6'-trideoxy-α-L-lyxo-hexapyranoside; |
| 15 | 3-glycoloyl-1,2,3,4,6,11-hexahydro-3,5,12-trihydroxy-10-methoxy-6,11-dioxo-1-naphthacenyl-3'-[3-acetoxy-1,3,5(10)-estratriene-17β-oxycarbonylmethyl]amino-2',3',6'-trideoxy-α-L-lyxo-hexapyranoside; |

| Test No. | Compounds used in tests in Table 18 |
|---|---|
| 16 | 3-glycoloyl-1,2,3,4,6,11-hexahydro-3,5,12-trihydroxy-10-methoxy-6,11-dioxo-1-naphthacenyl-3′-[3-propionyloxy-1,3,5(10)-estratriene-17β-oxycarbonylmethyl]amino-2′,3′,6′-trideoxy-α-L-lyxo-hexapyranoside; |
| 17 | 3-glycoloyl-1,2,3,4,6,11-hexahydro-3,5,12-trihydroxy-10-methoxy-6,11-dioxo-1-naphthacenyl-3′-[3-benzoyloxy-1,3,5-(10)-estratriene-17β-oxycarbonylmethyl]amino-2′,3′,6′-trideoxy-α-L-lyxo-hexapyranoside; |
| 18 | 3-acetyl-1,2,3,4,6,11-hexahydro-3,5,12-trihydroxy-10-methoxy-6,11-dioxo-1-naphthacenyl-3′-amino-2′,3′,6′-trideoxy-α-L-lyxo-hexapyranoside; |
| 19 | 3-acetyl-1,2,3,4,6,11-hexahydro-3,5,12-trihydroxy-10-methoxy-6,11-dioxo-1-naphthacenyl-3′-[3-hydroxy-1,3,5(10)-estratriene-17β-oxycarbonylmethyl]amino-2′,3′,6′-trideoxy-α-L-lyxo-hexapyranoside; |
| 20 | 2,4-bis(ethyleneimino)-6-(3-benzoyloxy-1,3,5(10)-estratriene-17β-oxycarbonylmethyloxyethyl)amino-s-triazine; |
| 21 | p-[bis(2-chloroethyl)amino]-L-phenyl alanine; |
| 22 | 3-benzoyloxy-1,3,5(10)-estratriene-17β-{p-[bis(2-chloroethyl)amino]-L-phenyl alaninyl}acetate. |

The typical steroid hormone-antitumor derivatives of the present invention are the novel compounds having the following formulas.

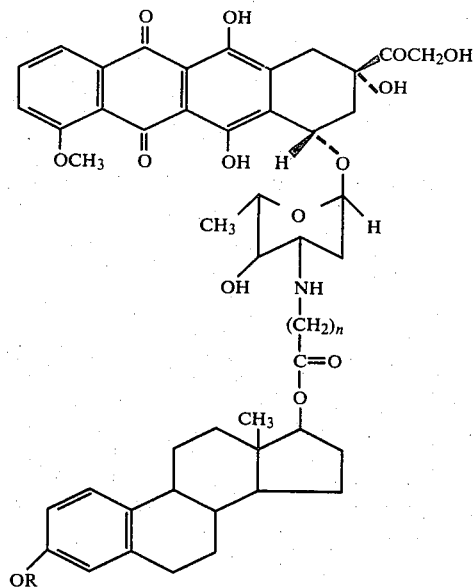

(I)

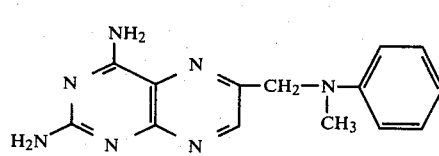

wherein R represents a hydrogen atom or an acyl group and n is an integer of 1 to 3.

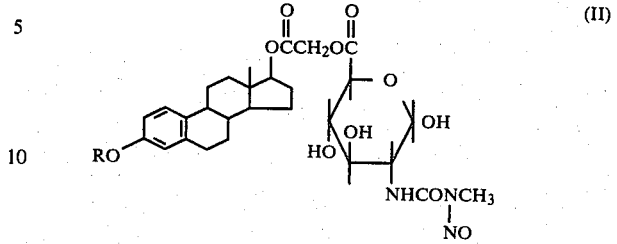

(II)

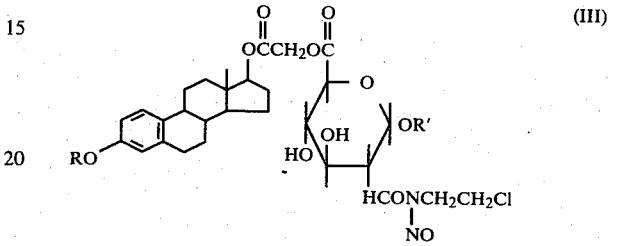

(III)

wherein R represents a hydrogen atom or an acyl group and R′ represents H or CH₃.

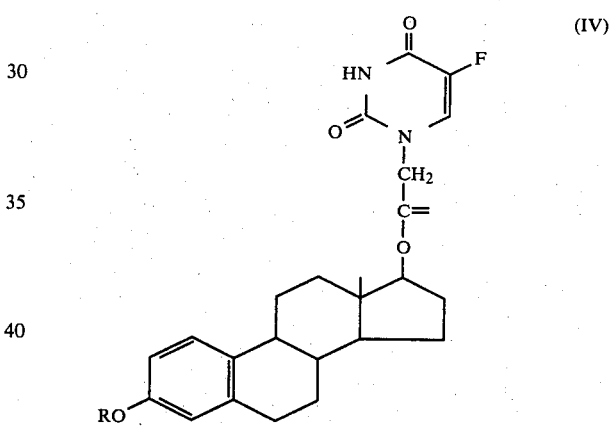

(IV)

wherein R represents a hydrogen atom or an acyl group.

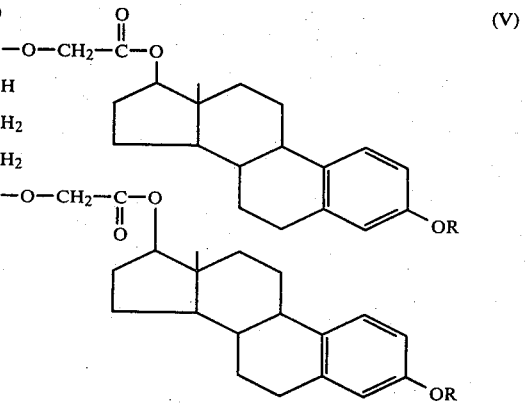

(V)

wherein R represents a hydrogen atom or an acyl group. The acyl group is preferably

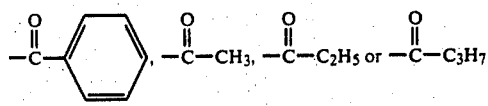

What is claimed is:
1. A compound of the formula:

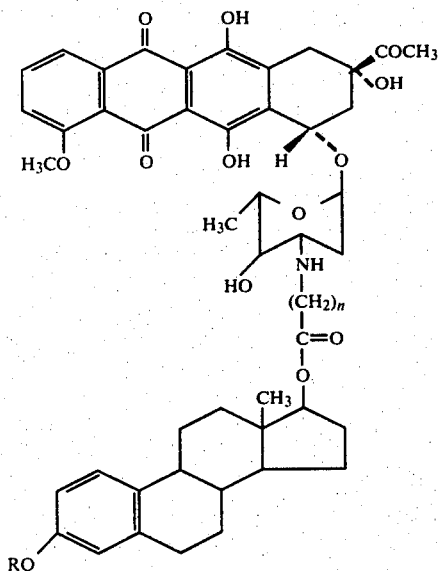

wherein R is hydrogen or acyl and n is an integer of 1 to 3.

2. A compound of the formula:

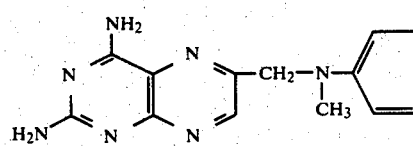

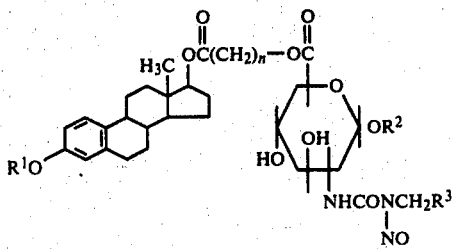

wherein $R^1$ is hydrogen or acyl, $R^2$ is hydrogen or methyl, $R^3$ is hydrogen or chloromethyl and n is an integer of 1 to 3.

3. A compound of the formula:

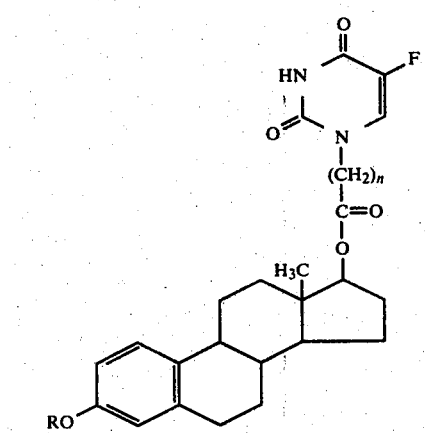

wherein R is hydrogen or acyl and n is an integer of 1 to 3.

4. A compound of the formula:

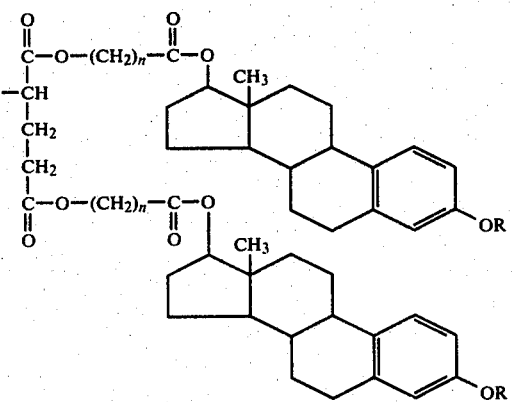

wherein R is hydrogen or acyl and n is an integer of 1 to 3.

5. The compound of claim 1, 2, 3 or 4, wherein said acyl is benzoyl, acetyl, propionyl or butyroyl.

* * * * *